(12) United States Patent
Wolfe et al.

(10) Patent No.: US 7,504,216 B2
(45) Date of Patent: Mar. 17, 2009

(54) BACTERIAL COUNTERSELECTABLE HYBRID SYSTEMS

(75) Inventors: Scot Andrew Wolfe, Winchester, MA (US); Xiangdong Meng, Shrewsbury, MA (US); Jae Keith Joung, Winchester, MA (US)

(73) Assignee: University of Massachusetts, Boston, MA (US)

( * ) Notice: Subject to any disclaimer, the term of this patent is extended or adjusted under 35 U.S.C. 154(b) by 268 days.

(21) Appl. No.: 11/050,174

(22) Filed: Feb. 2, 2005

(65) Prior Publication Data

US 2005/0287550 A1    Dec. 29, 2005

Related U.S. Application Data

(60) Provisional application No. 60/541,464, filed on Feb. 2, 2004.

(51) Int. Cl.
 *C12Q 1/68*     (2006.01)
 *C12Q 1/02*     (2006.01)
 *G01N 33/554*   (2006.01)
 *G01N 33/569*   (2006.01)
 *C12N 15/74*    (2006.01)

(52) U.S. Cl. .......................... 435/6; 435/7.32; 435/7.37; 435/29; 435/471

(58) Field of Classification Search ........................ None
See application file for complete search history.

(56) References Cited

U.S. PATENT DOCUMENTS

| 5,198,346 | A  | 3/1993 | Ladner et al. |
| 5,925,523 | A  | 7/1999 | Dove et al. |
| 6,200,759 | B1 | 3/2001 | Dove et al. |
| 2003/0044787 | A1 | 3/2003 | Joung et al. |

OTHER PUBLICATIONS

Walhout et al. (1999) Genome Res. 9:1128-1134.*
Bach et al., "Evidence for transcriptional regulation of orotidine-5'-phosphate decarboxylase in yeast by hybridization of mRNA to the yeast structural gene cloned in *Escherichia coli*," Proc. Natl. Acad. Sci. USA 76(1):386-90 (1979).
Broschard et al., "Mutagenic specificity of the food mutagen 2-amino-3-methylimidazo[4,5-f]quinoline in *Escherichia coli* using the yeast URA3 gene as a target," Carcinogenesis 19(2):305-10 (1998).
Datsenko and Wanner, "One-step inactivation of chromosomal genes in *Escherichia coli* K-12 using PCR products," Proc. Natl. Acad. Sci. USA 97(12):6640-645 (2000).
Dove and Hochschild, "Conversion of the omega subunit of *Escherichia coli* RNA polymerase into a transcriptional activator or an activation target," Genes Dev. 12(5):745-54 (1998).
Dove et al., "Activation of prokaryotic transcription through arbitrary protein-protein contacts," Nature 386:627-6390 (1997).
Fields and Song, "A novel genetic system to detect protein-protein interactions," Nature 340(6230):245-6 (1989).

Gstaiger et al., "A B-cell coactivator of octamer-binding transcription factors," Nature 373(6512):360-2 (1995).
Himmelfarb et al., "GAL11P: a yeast mutation that potentiates the effect of weak GAL4-derived activators," Cell 63(6):1299-1309 (1990).
Joung et al., "A bacterial two-hybrid selection system for studying protein-DNA and protein-protein interactions," Proc. Natl. Acad. Sci. USA 97(13):7382-387 (2000).
Kwang-Hee Bae et al., "Human zinc fingers as building blocks in the construction of artificial transcription factors," Nat. Biotechnol. 21(3):275-80 (2003).
Lanzer et al., "Promoters largely determine the efficiency of repressor action," Proc. Natl. Acad. Sci. USA 85(23):8973-977 (1988).
Le Douarin et al., "A new version of the two-hybrid assay for detection of protein-protein interactions," Nucleic Acids Res. 23(5):876-8 (1995).
Levine et al., "Inhibition of orotidine-5'-phosphate decarboxylase by 1-(5'-phospho-beta-d-ribofuranosyl)barbituric acid, 6-azauridine 5'-phosphate, and uridine 5'-phosphate," Biochemistry 19(22):4993-9 (1980).
Li and Hershkowitz, "Isolation of ORC6, a component of the yeast origin recognition complex by a one-hybrid system," Science 262(5141):1870-4 (1993).
Losson et al., "Cloning of a eukaryotic regulatory gene," Mol. Gen. Genet. 184(3):394-9 (1981).
Lutz and Bujard, "Independent and tight regulation of transcriptional units in *Escherichia coli* via the LacR/O, the TetR/O and AraC/I1-I2 regulatory elements," Nucleic Acids Res. 25(6):1203-10 (1997).
Makino et al., "DNA binding of PhoB and its interaction with RNA polymerase," J. Mol. Biol. 259(1):15-26 (1996).
Schell, "Molecular biology of the LysR family of transcriptional regulators," Annu. Rev. Microbiol. 47:597-626 (1993).
SenGupta et al., "A three-hybrid system to detect RNA-protein interactions in vivo," Proc. Natl. Acad. Sci. USA 93(16):8496-501 (1996).
Suzuki and Brenner, "Classification of multi-helical DNA-binding domains and application to predict the DBD structures of sigma factor, LysR, OmpR/PhoB, CENP-B, Rapl, and XylS/Ada/AraC," FEBS Lett. 372(2-3):215-21 (1995). Erratum in: FEBS Lett Mar. 4, 1996;381(3):270.
Tan, "A modular polycistronic expression system for overexpressing protein complexes in *Escherichia coli*," Protein Expr. Purif. 21(1):224-34 (2001).
Vidal et al., "Genetic characterization of a mammalian protein-protein interaction domain by using a yeast reverse two-hybrid system," Proc. Natl. Acad. Sci. USA 93(19):10321-6 (1996).
Vidal et al., "Reverse two-hybrid and one-hybrid systems to detect dissociation of protein-protein and DNA-protein interactions," Proc. Natl. Acad. Sci. USA 93(19):10315-20 (1996).
Wilson et al., "Identification of the DNA binding site for NGFI-B by genetic selection in yeast," Science 252(5010):1296-300 (1991).
Matchmaker Once-Hybrid System, CLONTECHniques, pp. 1-3 (1995).
BacterioMatch II Two-Hybrid System Vector Kit, Instruction Manual, Catalog #240065, Revision #113008, pp. 1-29.

* cited by examiner

*Primary Examiner*—Michael Burkhart
(74) *Attorney, Agent, or Firm*—Fish & Richardson P.C.

(57) ABSTRACT

The present application relates to the hybrid selection methods in prokaryotes using counterselectable reporter genes.

17 Claims, 16 Drawing Sheets

Original URA3 construct (RNA)
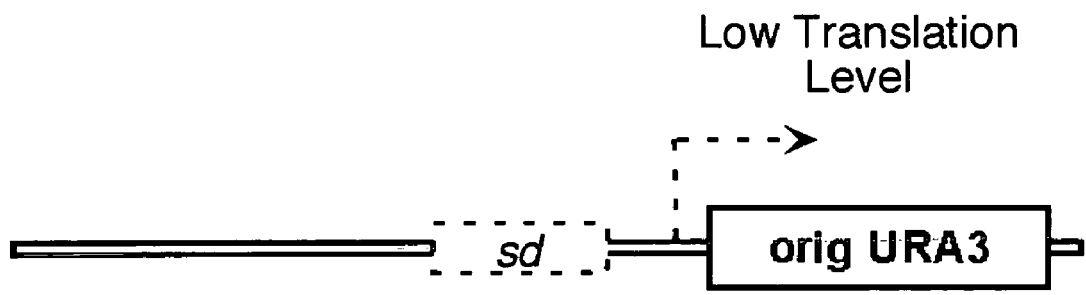
-TE or SD+ URA3 constructs
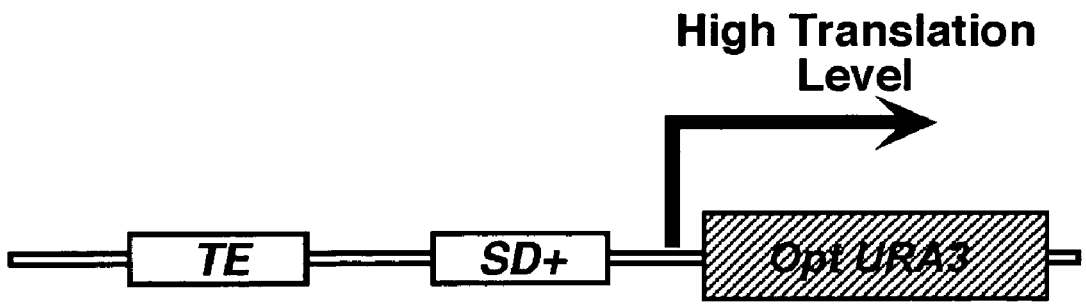
FIG. 3A

URA3 gene modifications

```
              10                  20                  30                  40                  50
URA3 opt   ATGTCTAAAGCTACATATAAGGAACGTGCTGCTACTCATCCTAGTCCTGT
URA3 orig  ATGTCTAAAGCTACATATAAGGAACGTGCTGCTACTCATCCTAGTCCTGT
           ATGTCTAAAGCTACATATAAGGAACGTGCTGCTACTCATCCTAGTCCTGT 60                  70                  80                  90                 100
URA3 opt   TGCTGCCAAGCTATTTAATATCATGCACGAAAAGCAAACAAACTTGTGTG
URA3 orig  TGCTGCCAAGCTATTTAATATCATGCACGAAAAGCAAACAAACTTGTGTG
           TGCTGCCAAGCTATTTAATATCATGCACGAAAAGCAAACAAACTTGTGTG 110                 120                 130                 140                 150
URA3 opt   CTTCATTGGATGTTCGTACCACCAAGGAATTACTGGAGTTAGTTGAAGCA
URA3 orig  CTTCATTGGATGTTCGTACCACCAAGGAATTACTGGAGTTAGTTGAAGCA
           CTTCATTGGATGTTCGTACCACCAAGGAATTACTGGAGTTAGTTGAAGCA 160                 170                 180                 190                 200
URA3 opt   TTAGGTCCCAAAATTTGTTTACTAAAAACACATGTGGATATCTTGACTGA
URA3 orig  TTAGGTCCCAAAATTTGTTTACTAAAAACACATGTGGATATCTTGACTGA
           TTAGGTCCCAAAATTTGTTTACTAAAAACACATGTGGATATCTTGACTGA 210                 220                 230                 240                 250
URA3 opt   TTTTTCCATGGAGGGCACAGTTAAGCCGCTAAAGGCATTATCCGCCAAGT
URA3 orig  TTTTTCCATGGAGGGCACAGTTAAGCC GCTA AGGC ATTAT CCGCCAAGT
           TTTTTCCATGGAGGGCACAGTTAAGCCGCTAAAGGCATTATCCGCCAAGT 260                 270                 280                 290                 300
URA3 opt   ACAATTTTTTACTCTTCGAAGACAGAAAATTTGCTGACATTGGTAATACA
URA3 orig  ACAATTTTTTACTCTTCGAAGACAGAAAATTTGCTGACATTGGTAATACA
           ACAATTTTTTACTCTTCGAAGACAGAAAATTTGCTGACATTGGTAATACA 310                 320                 330                 340                 350
URA3 opt   GTCAAATTGCAGTACTCTGCGGGTGTATACAGAATAGCAGAATGGGCAGA
URA3 orig  GTCAAATTGCAGTACTCTGCGGGTGTATACAGAATAGCAGAATGGGCAGA
           GTCAAATTGCAGTACTCTGCGGGTGTATACAGAATAGCAGAATGGGCAGA 360                 370                 380                 390                 400
URA3 opt   CATTACGAATGCACACGGTGTGGTGGGCCCAGGTATTGTTAGCGGTTTGA
URA3 orig  CATTACGAATGCACACGGTGTGGTGGGCCCAGGTATTGTTAGCGGTTTGA
           CATTACGAATGCACACGGTGTGGTGGGCCCAGGTATTGTTAGCGGTTTGA 410                 420                 430                 440                 450
URA3 opt   AGCAGGCGGCAGAAGAAGTAACAAAGGAACCTAGAGGCCTTTTGATGTTA
URA3 orig  AGCAGGCGGCAGAAGAAGTAACAAAGGAACCTAGAGGCCTTTTGATGTTA
           AGCAGGCGGCAGAAGAAGTAACAAAGGAACCTAGAGGCCTTTTGATGTTA 460                 470                 480                 490                 500
URA3 opt   GCAGAATTGTCATGCAAGGGCTCCCTATCTACTGGAGAATATACTAAGGG
URA3 orig  GCAGAATTGTCATGCAAGGGCTCCCTATCTACTGGAGAATATACTAAGGG
           GCAGAATTGTCATGCAAGGGCTCCCTATCTACTGGAGAATATACTAAGGG 510                 520                 530                 540                 550
URA3 opt   TACTGTTGACATTGCGAAGAGCGACAAAGATTTTGTTATCGGCTTTATTG
URA3 orig  TACTGTTGACATTGCGAAGAGCGACAAAGATTTTGTTATCGGCTTTATTG
           TACTGTTGACATTGCGAAGAGCGACAAAGATTTTGTTATCGGCTTTATTG 560                 570                 580                 590                 600
URA3 opt   CTCAAAGAGACATGGGTGGAAGAGATGAAGGTTACGATTGGTTGATTATG
URA3 orig  CTCAAAGAGACATGGGTGGAAGAGATGAAGGTTACGATTGGTTGATTATG
           CTCAAAGAGACATGGGTGGAAGAGATGAAGGTTACGATTGGTTGATTATG 610                 620                 630                 640                 650
URA3 opt   ACACCCGGTGTGGGTTTAGATGACAAGGGAGACGCATTGGGTCAACAGTA
URA3 orig  ACACCCGGTGTGGGTTTAGATGACAAGGGAGACGCATTGGGTCAACAGTA
           ACACCCGGTGTGGGTTTAGATGACAAGGGAGACGCATTGGGTCAACAGTA 660                 670                 680                 690                 700
URA3 opt   TAGAACCGTGGATGATGTGGTCTCTACAGGATCTGACATTATTATTGTTG
URA3 orig  TAGAACCGTGGATGATGTGGTCTCTACAGGATCTGACATTATTATTGTTG
           TAGAACCGTGGATGATGTGGTCTCTACAGGATCTGACATTATTATTGTTG 710                 720                 730                 740                 750
URA3 opt   GAAGAGGACTATTTGCAAAGGGAAGGGATGCTAAGGTAGAGGGTGAACGT
URA3 orig  GAAGAGGACTATTTGCAAAGGGAAGGGATGCTAAGGTAGAGGGTGAACGT
           GAAGAGGACTATTTGCAAAGGGAAGGGATGCTAAGGTAGAGGGTGAACGT 760                 770                 780                 790                 800
URA3 opt   TACAGAAAAGCAGGCTGGGAAGCATACCCTGCGTCGTTGCGGCCAGCAGAA
URA3 orig  TACAGAAAAGCAGGCTGGGAAGCATATTTGAGAAGATGCCGGCCAGCAAAA
           TACAGAAAAGCAGGCTGGGAAGCATAYYTGMGWMGWTGCGGCCAGCARAA 810                 820                 830                 840                 850
URA3 opt   CTAA
URA3 orig  CTAGTGA
           CTARTGA
```

FIG. 3B

```
GAGCGAAGCGTAGGCGTC
CAACGTTGTGTGGGCGTG
TGTAGTTGCGTGGGAGGG
CGATAATCCGGGGGCGTA
CGAGGATGCGGGGGTGTG
AATCGAGCGTGGGAGGGG
TTGCCCACGTGGGCGTG
GAATGTGTGTGGGCGGCT
ATTTGTAGCGTGGGCGAT
GCACGCCGCTTCCGTATG
ATCCACCCACGCGCTCAA
TGTAGTTGCGTGGGAGGG
TTGCCCCGCGTGGGCGTC
TTGTTGTGCGTAGGCGGC
TAACCCGCGTGGGCGTA
ATCGAGGGCGTGGGTGGC
```

```
AGCCCTACGCGTGGGTAG
AGCCTACGCGTGGGTAG
ACCACGTGTGGGGTCCTG
CCCACGCGGGGGCGCGGC
CCCCCACGCGTAGACAAC
GAGCACGCGGGACATCTA
GTCCACGCGTGCGAGCAA
GTGCACGCGTGGGATCTA
TAGCTTTACAACCGGGGAC
CCCCACGCGTGGTTAACC
CCCACGCGGGGCGCGGC
TGGGGCTGCGAGTATACT
TGCACGCGTGGGGTCCTG
GAGCACCCTGGGACATCA
AGCCTTTTGAGGGTTGGG
ACCACGCGTGGGGACAT
ATTATGCGGTTCTGCAGG
CGGCACGCGTGGGGGTGG
GATCTACGCGTGGGGGTC
TAGCTTTAGAACCGGGGAC
AGAGTGACTAAGTCAGT
ATCCCACGCCTGGGACG
ACCACGCGTGGGGGACAT
GCACGCGTGGGTATGT
```

FIG. 9A

Zif268-cFos in vivo SELEX alignment

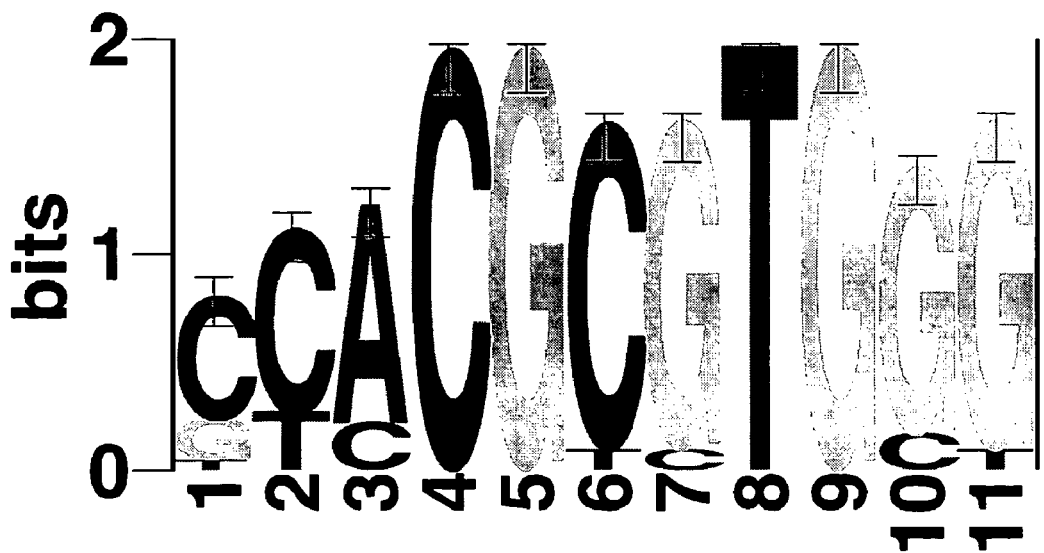

FIG. 9B

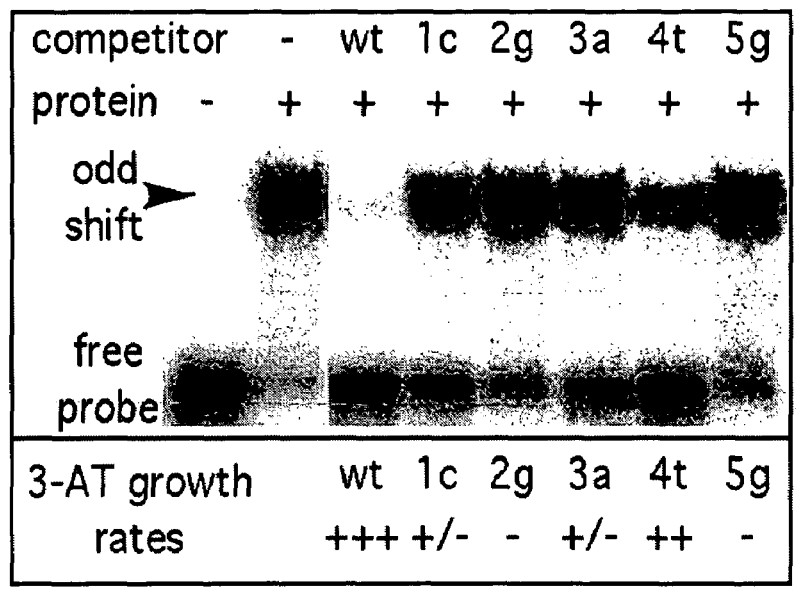
FIG. 13
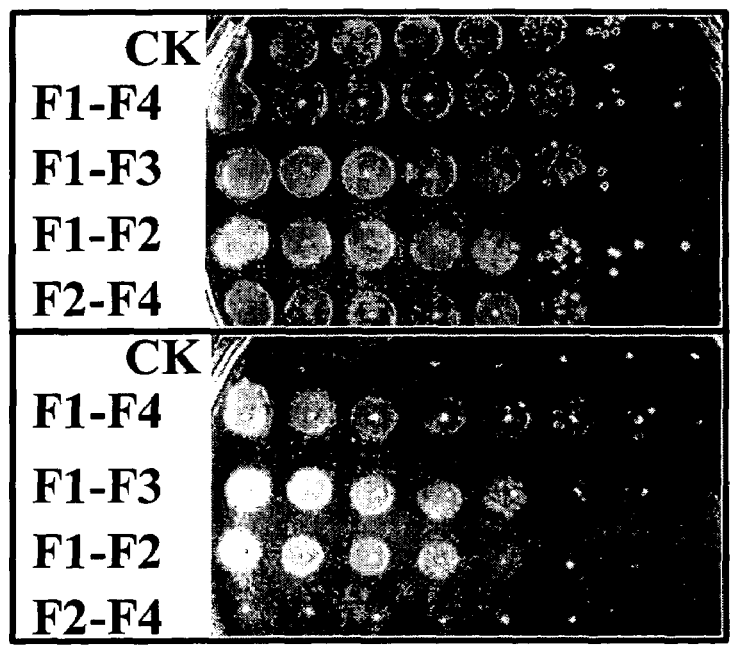
FIG. 14A
FIG. 14B

SEQUENCE LISTING

<160> NUMBER OF SEQ ID NOS: 57

<210> SEQ ID NO 1
<211> LENGTH: 17
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 8, 9, 10, 11, 12, 13
<223> OTHER INFORMATION: n = a, t, c or g

<400> SEQUENCE: 1

-continued ggrggccnnn nnnrggk                                                17

<210> SEQ ID NO 2
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 2
cccacgcgtg gg                                                     12

<210> SEQ ID NO 3
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 3
cacccgcggg tg                                                     12

<210> SEQ ID NO 4
<211> LENGTH: 11
<212> TYPE: DNA
<213> ORGANISM: Artificial Sequence
<220> FEATURE:
<223> OTHER INFORMATION: Synthetically generated oligonucleotide

<400> SEQUENCE: 4
ggcgtgggcg t                                                      11

<210> SEQ ID NO 5
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 5
mccacgcgtg gk                                                     12

<210> SEQ ID NO 6
<211> LENGTH: 11
<212> TYPE: DNA
<213> ORGANISM: Artificial Sequence
<220> FEATURE:
<223> OTHER INFORMATION: Synthetically generated oligonucleotide

<400> SEQUENCE: 6
kttcccacgs t                                                      11

<210> SEQ ID NO 7
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 7
ccacacccac gcagtaca                                               18

<210> SEQ ID NO 8
<211> LENGTH: 18
<212> TYPE: DNA
<213> ORGANISM: Artificial Sequence

```
<220> FEATURE:
<223> OTHER INFORMATION: Synthetically generated oligonucleotide

<400> SEQUENCE: 8
atgcttgtcg ctacgtgg                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 9
aacctcccac gcaggctg                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 10
ccgcctacgc aatgtcca                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 11
ttccgcccac acacgcgg                                                 18

<210> SEQ ID NO 12
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 12
cacgcccacg tggggcaa                                                 18

<210> SEQ ID NO 13
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 13
gacgcccaca cgtgcgag                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 14
cacgcccacg tggatagt                                                 18
```

<210> SEQ ID NO 15
<211> LENGTH: 807
<212> TYPE: DNA
<213> ORGANISM: Saccharomyces cerevisiae

<400> SEQUENCE: 15

| | |
|---|---|
| atgtctaaag ctacatataa ggaacgtgct gctactcatc ctagtcctgt tgctgccaag | 60 |
| ctatttaata tcatgcacga aaagcaaaca aacttgtgtg cttcattgga tgttcgtacc | 120 |
| accaaggaat tactggagtt agttgaagca ttaggtccca aaatttgttt actaaaaaca | 180 |
| catgtggata tcttgactga ttttccatg gagggcacag ttaagccgct aaaggcatta | 240 |
| tccgccaagt acaattttt actcttcgaa gacagaaaat tgctgacat tggtaataca | 300 |
| gtcaaattgc agtactctgc gggtgtatac agaatagcag aatgggcaga cattacgaat | 360 |
| gcacacggtg tggtgggccc aggtattgtt agcggtttga agcaggcggc agaagaagta | 420 |
| acaaaggaac ctagaggcct tttgatgtta gcagaattgt catgcaaggg ctccctatct | 480 |
| actggagaat atactaaggg tactgttgac attgcgaaga gcgacaaaga ttttgttatc | 540 |
| ggctttattg ctcaaagaga catgggtgga agagatgaag ttacgattg gttgattatg | 600 |
| acacccggtg tgggtttaga tgacaaggga gacgcattgg gtcaacagta tagaaccgtg | 660 |
| gatgatgtgg tctctacagg atctgacatt attattgttg gaagaggact atttgcaaag | 720 |
| ggaagggatg ctaaggtaga gggtgaacgt tacagaaaag caggctggga agcatatttg | 780 |
| agaagatgcg gccagcaaaa ctagtga | 807 |

<210> SEQ ID NO 16
<211> LENGTH: 804
<212> TYPE: DNA
<213> ORGANISM: Artificial Sequence
<220> FEATURE:
<223> OTHER INFORMATION: Synthetically generated oligonucleotide

<400> SEQUENCE: 16

| | |
|---|---|
| atgtctaaag ctacatataa ggaacgtgct gctactcatc ctagtcctgt tgctgccaag | 60 |
| ctatttaata tcatgcacga aaagcaaaca aacttgtgtg cttcattgga tgttcgtacc | 120 |
| accaaggaat tactggagtt agttgaagca ttaggtccca aaatttgttt actaaaaaca | 180 |
| catgtggata tcttgactga ttttccatg gagggcacag ttaagccgct aaaggcatta | 240 |
| tccgccaagt acaattttt actcttcgaa gacagaaaat tgctgacat tggtaataca | 300 |
| gtcaaattgc agtactctgc gggtgtatac agaatagcag aatgggcaga cattacgaat | 360 |
| gcacacggtg tggtgggccc aggtattgtt agcggtttga agcaggcggc agaagaagta | 420 |
| acaaaggaac ctagaggcct tttgatgtta gcagaattgt catgcaaggg ctccctatct | 480 |
| actggagaat atactaaggg tactgttgac attgcgaaga gcgacaaaga ttttgttatc | 540 |
| ggctttattg ctcaaagaga catgggtgga agagatgaag ttacgattg gttgattatg | 600 |
| acacccggtg tgggtttaga tgacaaggga gacgcattgg gtcaacagta tagaaccgtg | 660 |
| gatgatgtgg tctctacagg atctgacatt attattgttg gaagaggact atttgcaaag | 720 |
| ggaagggatg ctaaggtaga gggtgaacgt tacagaaaag caggctggga agcatacctg | 780 |
| cgtcgttgcg gccagcagaa ctaa | 804 |

<210> SEQ ID NO 17
<211> LENGTH: 807
<212> TYPE: DNA
<213> ORGANISM: Artificial Sequence
<220> FEATURE:
<223> OTHER INFORMATION: Synthetically generated oligonucleotide

<400> SEQUENCE: 17

```
atgtctaaag ctacatataa ggaacgtgct gctactcatc ctagtcctgt tgctgccaag      60
ctatttaata tcatgcacga aaagcaaaca aacttgtgtg cttcattgga tgttcgtacc     120
accaaggaat tactggagtt agttgaagca ttaggtccca aaatttgttt actaaaaaca     180
catgtggata tcttgactga tttttccatg gagggcacag ttaagccgct aaaggcatta     240
tccgccaagt acaattttt actcttcgaa gacagaaaat tgctgacat tggtaataca      300
gtcaaattgc agtactctgc gggtgtatac agaatagcag aatgggcaga cattacgaat     360
gcacacggtg tggtgggccc aggtattgtt agcggtttga agcaggcggc agaagaagta     420
acaaaggaac ctagaggcct tttgatgtta gcagaattgt catgcaaggg ctccctatct     480
actggagaat atactaaggg tactgttgac attgcgaaga gcgacaaaga ttttgttatc     540
ggctttattg ctcaaagaga catgggtgga agagatgaag gttacgattg gttgattatg     600
acacccggtg tgggtttaga tgacaaggga gacgcattgg gtcaacagta tagaaccgtg     660
gatgatgtgg tctctacagg atctgacatt attattgttg gaagaggact atttgcaaag     720
ggaagggatg ctaaggtaga gggtgaacgt tacagaaaag caggctggga agcatayytg     780
mgwmgwtgcg gccagcaraa ctartga                                          807
```

<210> SEQ ID NO 18
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 18

```
gagcgaagcg taggcgtc                                                    18
```

<210> SEQ ID NO 19
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 19

```
caacgttgtg tgggcgtg                                                    18
```

<210> SEQ ID NO 20
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 20

```
tgtagttgcg tgggaggg                                                    18
```

<210> SEQ ID NO 21
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 21

```
cgataatccg gggcgta                                                    18

<210> SEQ ID NO 22
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 22
cgaggatgcg ggggtgtg                                                   18

<210> SEQ ID NO 23
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 23
aatcgagcgt gggagggg                                                   18

<210> SEQ ID NO 24
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 24
ttgccccacg tgggcgtg                                                   18

<210> SEQ ID NO 25
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 25
gaatgtgtgt gggcggct                                                   18

<210> SEQ ID NO 26
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 26
atttgtagcg tgggcgat                                                   18

<210> SEQ ID NO 27
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 27
gcacgccgct tccgtatg                                                   18

<210> SEQ ID NO 28
<211> LENGTH: 18
<212> TYPE: DNA
<213> ORGANISM: Artificial Sequence
```

```
<220> FEATURE:
<223> OTHER INFORMATION: Synthetically generated oligonucleotide

<400> SEQUENCE: 28
atccacccac gcgctcaa                                                        18

<210> SEQ ID NO 29
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 29
tgtagttgcg tgggaggg                                                        18

<210> SEQ ID NO 30
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 30
ttgccccgcg tgggcgtc                                                        18

<210> SEQ ID NO 31
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 31
ttgttgtgcg taggcggc                                                        18

<210> SEQ ID NO 32
<211> LENGTH: 17
<212> TYPE: DNA
<213> ORGANISM: Artificial Sequence
<220> FEATURE:
<223> OTHER INFORMATION: Synthetically generated oligonucleotide

<400> SEQUENCE: 32
taacccgcgt gggcgta                                                         17

<210> SEQ ID NO 33
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 33
atcgagggcg tgggtggc                                                        18

<210> SEQ ID NO 34
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 34
agccctacgc gtgggtag                                                        18
```

<210> SEQ ID NO 35
<211> LENGTH: 17
<212> TYPE: DNA
<213> ORGANISM: Artificial Sequence
<220> FEATURE:
<223> OTHER INFORMATION: Synthetically generated oligonucleotide

<400> SEQUENCE: 35
agcctacgcg tgggtag                                               17

<210> SEQ ID NO 36
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 36
accacgtgtg gggtcctg                                              18

<210> SEQ ID NO 37
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 37
cccacgcggg ggcgcggc                                              18

<210> SEQ ID NO 38
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 38
cccccacgcg tagacaac                                              18

<210> SEQ ID NO 39
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 39
gagcacgcgg gacatcta                                              18

<210> SEQ ID NO 40
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 40
gtccacgcgt gcgagcaa                                              18

<210> SEQ ID NO 41
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 41
gtgcacgcgt gggatcta                                                        18

<210> SEQ ID NO 42
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 42
tagctttaca accggggac                                                       19

<210> SEQ ID NO 43
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 43
ccccacgcgt ggttaacc                                                        18

<210> SEQ ID NO 44
<211> LENGTH: 17
<212> TYPE: DNA
<213> ORGANISM: Artificial Sequence
<220> FEATURE:
<223> OTHER INFORMATION: Synthetically generated oligonucleotide

<400> SEQUENCE: 44
cccacgcggg gcgcggc                                                         17

<210> SEQ ID NO 45
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 45
tggggctgcg agtatact                                                        18

<210> SEQ ID NO 46
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 46
tgcacgcgtg gggtcctg                                                        18

<210> SEQ ID NO 47
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 47
gagcaccctg ggacatca                                                        18

<210> SEQ ID NO 48

-continued

```
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 48 agcctttga gggttggg                                                  18

<210> SEQ ID NO 49
<211> LENGTH: 17
<212> TYPE: DNA
<213> ORGANISM: Artificial Sequence
<220> FEATURE:
<223> OTHER INFORMATION: Synthetically generated oligonucleotide

<400> SEQUENCE: 49
accacgcgtg gggacat                                                  17

<210> SEQ ID NO 50
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 50
attatgcggt tctgcagg                                                 18

<210> SEQ ID NO 51
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 51
cggcacgcgt gggggtgg                                                 18

<210> SEQ ID NO 52
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 52
gatctacgcg tgggggtc                                                 18

<210> SEQ ID NO 53
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 53
tagctttaga accggggac                                                19

<210> SEQ ID NO 54
<211> LENGTH: 17
<212> TYPE: DNA
<213> ORGANISM: Artificial Sequence
<220> FEATURE:
<223> OTHER INFORMATION: Synthetically generated oligonucleotide

<400> SEQUENCE: 54
```

```
agagtgacta agtcagt                                              17

<210> SEQ ID NO 55
<211> LENGTH: 17
<212> TYPE: DNA
<213> ORGANISM: Artificial Sequence
<220> FEATURE:
<223> OTHER INFORMATION: Synthetically generated oligonucleotide

<400> SEQUENCE: 55
atcccacgcc tgggacg                                              17

<210> SEQ ID NO 56
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 56
accacgcgtg ggggacat                                             18

<210> SEQ ID NO 57
<211> LENGTH: 16
<212> TYPE: DNA
<213> ORGANISM: Artificial Sequence
<220> FEATURE:
<223> OTHER INFORMATION: Synthetically generated oligonucleotide

<400> SEQUENCE: 57
gcacgcgtgg gtatgt                                               16
```

BACTERIAL COUNTERSELECTABLE HYBRID SYSTEMS

CROSS-REFERENCE TO RELATED APPLICATIONS

This application claims priority to U.S. Provisional Patent Application Ser. No. 60/541,464, filed on Feb. 2, 2004, the contents of which is hereby incorporated by reference in its entirety.

TECHNICAL FIELD

This invention relates to hybrid selection methods.

BACKGROUND

The two-hybrid system was developed as a tool to identify the interactions between molecules such as DNA, RNA, or proteins, utilizing eukaryotic cells (Fields and Song (1989) Nature, 340:245-246). Two-hybrid systems that utilize positive selection in bacterial cells have been described (e.g., U.S. Pat. No. 5,925,523).

SUMMARY OF THE INVENTION

The present invention relates to methods for determining whether molecules interact with one another using a counterselectable assay in prokaryotic cells. The molecules can be DNA, RNA, proteins, or other small molecules. The use of a combination of a positive and a negative selectable markers in the serial analysis of clones can provide a great reduction in the number of false positives (noise) that are obtained as an end result when compared with a positive selectable marker alone. The present invention also relates to methods for identifying compounds that interfere with molecular interactions.

Accordingly, the invention relates to, for example, methods for determining whether test DNA molecules interacts with test polypeptides or proteins. The methods include (a) providing a first population of prokaryotic host cells, wherein at least one of the host cells comprises; (i) a reporter vector comprising a selectable reporter gene and a counterselectable reporter gene, wherein the selectable reporter gene and the counterselectable reporter gene are operably linked to a test DNA molecule; and (ii) a chimeric gene that encodes a fusion protein comprising a test polypeptide fused to a gene activating domain, wherein interaction of the test DNA molecule and the test polypeptide in the host cell results in an increase in expression of the selectable reporter gene and of the counterselectable reporter gene.

The methods further include (b) maintaining the first population of host cells under selective conditions that allow cell growth as a result of the expression of the selectable reporter gene; (c) isolating the reporter vectors from cells of the first population of host cells that grow under the selective conditions; (d) introducing the isolated reporter vectors into a second population of host cells that lack the chimeric gene; (e) maintaining the second population of host cells under counterselective conditions that inhibit cell growth as a result of the expression of the counterselectable reporter gene; and (f) measuring growth of the second population of host cells, wherein an ability to survive under counterselective conditions indicates that the test DNA molecule has interacted with the test polypeptide.

These methods can further include identifying a test DNA molecule that interacts with the test polypeptide, the method comprising isolating a reporter vector from a cell of the second population of host cells that grow under the counterselective conditions; and determining the sequence of the test DNA molecule in the reporter vector. In these methods, the test DNA molecule can be a random DNA sequence or can be taken from a nucleic acid library. The host cells may lack a functional endogenous gene that is homologous to the selectable reporter gene, e.g., lack a functional endogenous hisB gene, and/or the host cells may lack a functional endogenous gene that is homologous to the counterselectable reporter gene, such as lacking a functional endogenous pyrF gene.

In these methods, and all the methods described herein, the host cells can be bacterial US0 cells, the selectable reporter gene can be a LEU2, TRP1, or HIS3 gene, the selective conditions can include maintaining the host cells in medium lacking histidine, and the selective conditions can further include maintaining the host cells in medium containing 3-amino-1,2,4-triazole (3-AT). In certain embodiments, the counterselectable reporter gene can be a URA3, LYS2, GAL1, CYH2, sacB, or CAN1 gene, and counterselective conditions can include maintaining the host cells in medium containing uracil and 5-fluoro orotic acid (5-FOA).

Furthermore, the reporter genes in all the methods, vectors, and libraries described herein can encode a gene product that provides at least one detectable signal selected, such as color, fluorescence, luminscence, a cell surface tag, cell viability, relief of a cell nutritional requirement, cell growth, or drug resistance. The reporter genes can also encode a gene product such as a spectinomycin resistance gene product, a streptomycin resistance gene product, chloramphenicol acetyl transferase, luciferase, β-galactosidase, or alkaline phosphatase. The host cells can be a strain of Escherichia, Bacillus, Streptomyces, Pseudomonas, Salmonella, Serratia, or Shigella.

In certain embodiments, the gene activating domain can include the α domain of a RNA polymerase, or other DNA dependent RNA polymerases such as a T7 RNA polymerase, and the test DNA molecules used in the new methods can be between about 5 bp and about 100 kb in size.

In various embodiments of the new methods, the selectable reporter gene and the counterselectable reporter gene are both operably linked to a lac promoter, and the reporter vector can be integrated into the F'-episome of the host cell. The reporter vector can also include an origin of replication, e.g., one that limits expression of the reporter vector to not more than 50 or 10 copies, or a phage f1 origin of replication. The reporter vector can also include an independent Shine-Dalgarno sequence located between the selectable reporter gene and the counterselectable reporter gene. In certain embodiments, at least one of the selectable reporter gene or the counterselectable reporter gene can be derived from a eukaryote and in which gene at least one codon has been modified to a preferred bacterial codon.

In some of the new methods, the steps can be rearranged such that the counterselection steps are done before the selection steps. For example, in another aspect, the invention features methods for determining whether a test nucleic acid molecule interacts with a test polypeptide by (a) providing a first population of prokaryotic host cells, wherein at least one of the host cells includes a reporter vector comprising a selectable reporter gene and a counterselectable reporter gene, wherein the selectable reporter gene and the counterselectable reporter gene are operably linked to a test DNA molecule; (b) maintaining the first population of host cells under counterselective conditions that inhibit cell growth as a result of the expression of the counterselectable reporter gene; (c) isolating the reporter vectors from cells of the first population of host cells that grow under the counterselective conditions; (d) providing a second population of prokaryotic host cells, wherein at least one of the host cells includes a chimeric gene that encodes a fusion protein including a test polypeptide fused to a gene activating domain, wherein interaction of the test DNA molecule and the test polypeptide in the host cell results in an increase in expression of the selectable reporter gene and of the counterselectable reporter gene; (e) introducing the isolated reporter vectors into the second population of host cells; (f) maintaining the second population of host cells under selective conditions that allow cell growth as a result of the expression of the selectable reporter gene; and (g) measuring growth of the second population of host cells, wherein an ability to survive under selective conditions indicates that the test DNA molecule has interacted with the test polypeptide.

In these methods the reporter vectors isolated in step (c) represent a rarified library as described herein. These rarified library can be used to abbreviate the various methods described herein, for example, they can be used with only selective conditions.

In another aspect, the invention includes the prokaryotic host cells used in the new methods. For example, the invention features prokaryotic cells having one or more exogenous counterselectable reporter genes, e.g., integrated into their genomes or on separate vectors or plasmids, that are operably linked to one or more promoters including a DNA binding recognition site, wherein the prokaryotic cells lack a functional gene that is homologous to the exogenous counterselectable reporter genes. In these cells, the counterselectable reporter genes can be a URA3, LYS2, GAL1, CYH2, sacB, or CAN1 gene, and cells can be bacterial US0 cells, e.g., ones that lack a functional pyrF gene.

The invention also features libraries including a plurality of prokaryotic cells or colonies of prokaryotic cells, wherein each cell contains a reporter vector including a selectable reporter gene, a counterselectable reporter gene, and a DNA molecule, wherein the selectable reporter gene and the counterselectable reporter gene are operably linked to the DNA molecule, and wherein each cell or each colony of cells includes a different DNA molecule. These libraries of cells can be maintained under counterselective conditions to produce a rarified library of cells or colonies of cells that grow under counterselective conditions. For example, the counterselectable reporter gene can be URA3 and the counterselective conditions can include maintaining the host cells in medium that includes uracil and 5-fluoro orotic acid (5-FOA). In these libraries, the counterselectable reporter genes can be as described herein.

In another aspect, the invention also features reporter vectors used in the new methods. For example, the invention includes vectors that include a selectable reporter gene and a counterselectable reporter gene, wherein the selectable reporter gene and the counterselectable reporter gene are operably linked to a promoter; and a DNA sequence insertion site upstream of the promoter, wherein the DNA sequence insertion site is positioned to enable binding of a DNA binding domain to a DNA sequence to drive expression of the reporter genes.

These vectors can further include independent Shine-Dalgarno sequences before the translational start site of the selectable reporter gene and the counterselectable reporter gene. The counterselectable reporter genes in these vectors can be URA3, LYS2, GAL1, CYH2, sacB, and/or CAN1 genes.

The new vectors described herein can all include drug resistance genes, phage f1 origins of replication, and origins of replication such as p15A, Col E1, F' episome, and pSC101, and the origin of replication can be used to limit expression of the vector to not more than 25, 20, 15, 10, 5, or 1 copies within a host cell. In some embodiments, at least one of the selectable reporter gene or the counterselectable reporter gene is of eukaryotic origin and in which gene at least one codon has been altered to a preferred bacterial codon, and the order of the selectable and counterselectable genes can be changed.

In yet another aspect, the invention features kits that include one of the prokaryotic cell libraries described herein; and one or more vectors for encoding a fusion protein. These vectors include transcriptional and translational elements that direct expression of the fusion protein in a prokaryotic host cell; a DNA sequence that encodes a gene activation domain that is functionally associated with the transcriptional and translational elements of the vector; and one or more sites for inserting a DNA sequence encoding a test polypeptide into the vector in such a manner that the test polypeptide is expressed in-frame as part of the fusion protein containing the gene activation domain. The vectors can also include antibiotic resistance markers or origins of replication.

The prokaryotic cells in the libraries can be selected not to grow under selective conditions, but to grow under counterselective conditions absent interaction of the test polypeptide with a test DNA. In certain embodiments, the cells in the library lack a functional endogenous gene that is homologous to the selectable reporter gene and/or lack a functional endogenous gene that is homologous to the counterselectable reporter gene.

Other new kits include kits for detecting determining whether a first test protein interacts with a second test protein. These kits include a first vector for encoding a first fusion protein, the first vector including; (i) transcriptional and translational elements that direct expression of the first fusion protein in a prokaryotic host cell; (ii) a DNA sequence that encodes a DNA binding domain that is functionally associated with the transcriptional and translational elements of the first vector; and (iii) one or more insertion sites for inserting a DNA sequence encoding a first test protein into the first vector in such a manner that the first test protein is expressed in-frame as part of the first fusion protein containing the DNA binding domain.

These kits also include a second vector for encoding a second fusion protein, the second vector including; (i) transcriptional and translational elements that direct expression of the second fusion protein in a prokaryotic host cell; (ii) a DNA sequence that encodes a gene activation domain that is functionally associated with the transcriptional and translational elements of the second vector; and (iii) one or more insertion sites for inserting a DNA sequence encoding a second test protein into the second vector in such a manner that the second test protein is expressed in-frame as part of the second fusion protein containing the gene activation domain.

These kits also include a prokaryotic host cell containing a counterselectable reporter gene having a DNA binding site for the DNA binding domain, wherein the counterselectable reporter gene expresses a detectable transcript or protein when the first and second test proteins interact.

In another aspect, the invention includes methods for determining whether a first test polypeptide does or does not interact with a second test polypeptide. In some embodiments, these methods include (a) providing a prokaryotic host cell that includes (i) a counterselectable reporter gene operably linked to a transcriptional regulatory sequence that includes a DNA binding site for a DNA binding domain; (ii) a first chimeric gene that encodes a first fusion protein, the first fusion protein including the first test polypeptide fused to the DNA binding domain; and (iii) a second chimeric gene that encodes a second fusion protein, the second fusion protein including the second test polypeptide fused to a gene activating domain, wherein interaction of the first test polypeptide and the second test polypeptide in the host cell results in an increase in expression of the reporter gene.

The methods also include (b) providing a control prokaryotic host cell that contains (i) a counterselectable reporter gene operably linked to a transcriptional regulatory sequence that includes a DNA binding site for a DNA binding domain; and, optionally (ii) the first chimeric gene or the second chimeric gene, but not both; (c) growing the host cell and control host cell under counterselective conditions; and (d) measuring growth of the host cell, wherein a decrease in growth as compared to the growth of a control host cell indicates an interaction of the first test polypeptide and the second test polypeptide, and no change in growth indicates no interaction of the first test polypeptide and the second test polypeptide.

In some embodiments, one can use the new methods to screen for prey proteins that interact with a test polypeptide ("bait protein"), and use the counterselectable reporter genes to remove false positive prey proteins that self-activate promoters independent of the test polypeptides.

In these methods, at least one of the first and second test proteins, peptides, or polypeptides can be encoded by nucleic acids from a nucleic acid library, such as a eukaryotic cDNA library, a eukaryotic genomic library, a prokaryotic genomic library, a random library, a semi-random library, a viral genomic library, and an archeal genomic library.

These methods can also use host cells that further include one or more selectable reporter genes operably linked to a transcriptional regulatory sequence that includes a DNA binding site for a DNA binding domain, and can include the further steps of growing the host cells under selective conditions and measuring growth of the host cells, wherein survival of the host cells as compared to absence of growth of a control host cell that lacks a functional endogenous gene that is homologous to the selectable reporter grown under selective conditions indicates interaction of the first test polypeptide and the second test polypeptide.

For example, in these, and all the methods described herein, the selective conditions can include growing the host cell in medium lacking uracil, and further include growing the host cell in medium comprising 6-azauracil (6AU). The prokaryotic host cells can lack a functional pyrF gene, the counterselectable reporter gene can include a URA3 reporter gene, the host cell can be maintained in medium including uracil and 5-FOA; and a decrease in host cell growth as compared to the growth of a control host cell grown under identical medium conditions can indicate interaction of the first test protein and the second test protein. The methods can further include growing the host cells in medium lacking uracil, wherein an increase in host cell growth compared to the growth of a control host cell grown in medium lacking uracil, indicates interaction of the first test protein and the second test protein. The methods can further include growing the host cells in medium comprising 6-azauracil (6AU).

In another aspect, the new methods can be used to determine whether a test compound disrupts binding between the first test polypeptide protein and the second test polypeptide by further steps, including contacting the host cell with a test compound under counterselective conditions; and measuring the growth of the host cell, wherein an increase in cell growth as compared to the growth of the control host cell not contacted with the test compound indicates that the test compound disrupts the binding between the first test polypeptide and the second test polypeptide. The test compounds can be proteins, such as proteins encoded by a nucleic acid contained within a nucleic acid library, or they can be, for example, small organic or inorganic molecules, peptides, peptidomimetics, nucleotide sequences, oligosaccharides, and other oligomers.

In another aspect, the invention features methods for determining whether a test RNA molecule interacts with a test protein. These methods include (a) providing a prokaryotic host cell that includes (i) a counterselectable reporter gene operably linked to a transcriptional regulatory sequence that includes a DNA binding site for a DNA binding domain; (ii) a first chimeric gene that encodes a fusion RNA molecule, the fusion RNA molecule including the test RNA molecule fused to a non-random RNA molecule; (iii) a second chimeric gene that encodes a first fusion protein, the first fusion protein including the DNA binding domain that specifically binds to the DNA binding site, the DNA binding domain being fused to an RNA binding domain, wherein the RNA binding domain specifically binds to the non-random RNA molecule; and (iv) a third chimeric gene that encodes a second fusion protein, the second fusion protein including the test protein fused to a gene activating domain, wherein interaction of the test RNA molecule and the test protein in the host cell results in an increase in expression of the reporter gene.

The methods also include (b) growing the host cell under counterselective conditions; and (c) measuring growth of the host cell, wherein a decrease in host cell growth as compared to the growth of a control host cell lacking the first chimeric gene grown under counterselective conditions indicates interaction of the test RNA molecule and the test protein.

In another method for determining whether a first test RNA molecule interacts with a second test RNA molecule, the method includes (a) providing a prokaryotic host cell that include (i) a counterselectable reporter gene operably linked to a transcriptional regulatory sequence that includes a DNA binding site for a DNA binding domain; (ii) a first chimeric gene that encodes a first fusion RNA molecule, the first fusion RNA molecule comprising the first test RNA molecule fused to a first non-random RNA molecule; (iii) a second chimeric gene that encodes a first fusion protein, the first fusion protein comprising a DNA binding domain that specifically binds to the DNA binding site, the DNA binding domain being fused to a first RNA binding domain, wherein the first RNA binding domain specifically binds to the first non-random RNA molecule; (iv) a third chimeric gene that encodes a second fusion RNA molecule, the second fusion RNA molecule comprising the second test RNA molecule fused to a second non-random RNA molecule; and (v) a fourth chimeric gene that encodes a second fusion protein, the second fusion protein comprising a second RNA binding domain that specifically binds to the second non-random RNA molecule, the second binding domain being fused to a gene activating domain, wherein interaction of the first test RNA molecule and the second test RNA molecule in the host cell results in an increase in expression of the reporter gene This method also includes (b) growing the host cell under counterselective conditions; and (c) measuring growth of the host cell, wherein a decrease in host cell growth as compared to the growth of a control host cell not grown under counterselective conditions indicates interaction of the first test RNA molecule and the second test RNA molecule.

In these methods, the test RNA molecule can include a randomly generated RNA sequence, and the size of the test RNA molecule can be between about 0.5 and about 10 kb or about 5 bp to 35 bp, 10 bp to 500 bp. The prokaryotic host cells can further include a vector having the first, second, third, and/or fourth chimeric genes. The test RNA molecule comprises a randomly generated RNA sequence.

In another aspect, the invention features methods for determining whether test DNA molecules interact with test polypeptides by (a) providing a prokaryotic host cell that includes (i) a counterselectable reporter gene operably linked to the test DNA molecule (such as a random DNA sequence); (ii) a chimeric gene that encodes a fusion protein, the fusion protein including the test polypeptide (such as a random peptide) fused to a gene activating domain, wherein interaction of the test DNA molecule and the test polypeptide results in an increase in expression of the reporter gene; (b) growing the host cell under counterselective conditions; and (c) measuring growth of the host cell, wherein a decrease in host cell growth as compared to the growth of a control host cell lacking the chimeric gene and grown under counterselective conditions indicates interaction of the test DNA molecule and the test polypeptide.

The invention also includes methods for determining whether test DNA molecules interact with test proteins by (a) providing a prokaryotic host cell that includes (i) a counterselectable reporter gene operably linked to the test DNA molecule; (ii) a first chimeric gene that encodes a first fusion protein including the test protein, wherein the test protein comprises a DNA binding domain fused to a fragment of Gal11P; (iii) a second chimeric gene that encodes a second fusion protein including an α subunit of RNA polymerase fused to a Gal4 dimerization domain; (b) growing the host cell under counterselective conditions; and (c) measuring expression of the reporter gene, wherein a decrease in the expression of the reporter gene as compared to a control host cell lacking either the first or second chimeric genes, or lacking both chimeric genes, and grown under counterselective conditions indicates interaction of the test DNA molecule and the test protein.

Other embodiments are described throughout the specification and in the claims and include host cells, vectors, kits, and other methods related to the use of counterselection in a bacterial hybrid system.

Two sequences, e.g., nucleotide or amino acid sequences, are "fused" when they are joined by covalent bonds. The two sequences can be fused directly, e.g., the sequences can be immediately contiguous, or the sequences can be fused indirectly, e.g., the sequences can be separated by stretches of one or more nucleotides or amino acids within the same fusion RNA or DNA molecule or fusion protein.

A "protein," "polypeptide," or "peptide" is any chain of two or more amino acids linked by peptide bonds, regardless of length or post-translational modifications, such as glycosylation, amidation, or phosphorylation. Thus, these terms "protein," "polypeptide," and "peptide" are used interchangeably herein, unless otherwise noted. Proteins, polypeptides, and peptides may include one or more unnatural amino acids.

A gene and a regulatory sequence or sequences, e.g., a promoter, are "operably linked" when they are connected in such a way as to permit gene expression when the appropriate molecules, e.g., transcriptional activator proteins or proteins that include gene activating domains, are bound to the regulatory sequence or sequences.

A "randomly generated" sequence is a nucleic acid or amino acid sequence having no predetermined, or naturally occurring sequence. Randomly generated sequences can be derived from a nucleic acid library. An "intentionally designed" sequence is a sequence that has a DNA, RNA, or amino acid sequence or motif that is determined prior to its synthesis.

A "mutated" sequence is a sequence (nucleic acid or amino acid) that is altered relative to a reference, e.g., a wild-type sequence. The mutation can be generated using methods known in the art, e.g., by site-directed or random mutagenesis. Mutated sequences include those sequences that have point mutations, insertions, deletions, or rearrangements.

A "promoter" is a nucleotide sequence sufficient to direct transcription of a gene. A promoter can be located 5', 3', or within a coding region of a gene.

A nucleic acid "library" is a set of five or more DNA molecules. Such a library can include hundreds, thousands, millions, or more different DNA molecules.

"Bait" and "prey," as used herein, refer to molecules whose interaction is being tested. The "bait" is typically a known protein, DNA sequence, or RNA sequence, while the potential interacting molecule is the "prey." For example, in methods for determining the interaction of a DNA molecule with a protein, the known DNA molecule is a "bait nucleotide sequence" and a protein is a "prey polypeptide." Conversely, a known DNA binding protein is a "bait polypeptide" while a potential interacting nucleotide sequence is the "prey." In methods for determining the interaction of two proteins, a first protein, the known protein of interest, is a "bait polypeptide" and a second protein is a "prey polypeptide." In methods for determining the interaction of an RNA molecule and a protein, the known RNA molecule is a "bait RNA molecule" and a protein is a "prey polypeptide." In methods for determining the interaction of two RNA molecules, a first RNA molecule, the known RNA sequence of interest, is a "bait RNA molecule" and a second RNA molecule is a "prey RNA molecule." The "prey" can be a member of a library of molecules, for example, a cDNA library or a library of randomized oligonucleotides.

A chimeric gene encodes a fusion protein. The fusion protein of the chimeric gene can include a DNA binding protein (e.g., a test polypeptide); thus, the chimeric gene can include a nucleotide sequence or vector encoding a DNA binding protein (i.e., a DNA binding protein expression vector). The fusion protein of the chimeric gene can also include a gene activating domain; thus, the chimeric gene can include a nucleotide sequence or vector that encodes a gene activation protein (i.e., a gene activation protein expression vector). For example, a chimeric gene encoding both of these vectors can be used in assays for identifying DNA/protein interactions. Alternatively, in practicing the methods described herein, a first chimeric gene can include a DNA binding protein expression vector and a second chimeric gene can include a gene activating protein expression vector that encodes a gene activation domain; that is, more than one chimeric gene can be used to practice the methods.

A "vector" can include a nucleic acid sequence that encodes a polypeptide of interest (e.g., a DNA binding protein or a gene activating domain). Such nucleic acids can be inserted into another nucleotide sequence (e.g., into a plasmid) or can be fused with at least one other nucleic acid sequence (e.g., to generate a chimeric gene).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

BRIEF DESCRIPTION OF THE DRAWINGS

FIG. 3A is a schematic drawing indicating the changes to the original URA3 construct.

FIG. 3B is a sequence comparison of the original URA3 reporter gene (URA3 orig) (SEQ ID NO:15), the modified URA3 gene (URA3 opt) (SEQ ID NO:16), and their consensus Sequence (SEQ ID NO:17).

FIG. 9A is a list of raw unique sequences, SEQ ID Nos: 34-57 respectively, from the Zif268-cFos in vivo double selection experiments.

FIG. 9B is a sequence logo display of information content at each position in the binding site for 17 of the 24 sequences aligned by MEME.

FIG. 12 is a series of three sequence logos of Odd-skipped (Odd) signatures obtained at concentrations of 1.5, 2.5, and 5 mM 3-AT.

FIG. 13 is a representation of a gel shift assay and a growth rate table. The top panel shows gel shift competition assays. The bottom panel shows growth rates for bacteria with wild type or mutant prey in the presence of the Odd bait at 2 mM 3-AT.

FIGS. 14A and 14B are representations of growth plates showing truncation analysis of Odd-skipped to define the zinc fingers involved in DNA recognition. The top panel (FIG. 14A) is a titration of cells on minimal media plates. The bottom panel (FIG. 14B) is the same titration of cells on plates that contain selective media (3-AT).

FIG. 15A shows the results after the first round of selection; FIG. 15B shows the results after the second round of selection.

DETAILED DESCRIPTION

Figure 1A:
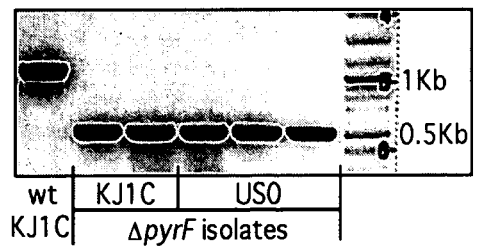
FIG. 1A is a representation of an image of PCR analysis of the pyrF gene in a wild-type KJ1C bacterial strain and two bacterial strains (KJ1C and US0) in which the pyrF gene has been deleted.

The invention employs new methods for determining interactions between molecules, by using counterselectable genes in prokaryotes. The new methods include a one hybrid system in which various interactions, e.g., the interaction between a DNA molecule and a protein, can be assayed using counterselection in prokaryotic cells. The methods also include multiple hybrid systems in which, e.g., the interaction between two proteins, between an RNA molecule and a protein, and between two RNA molecules, can be determined using counterselection in prokaryotic cells. The methods can be used, for example, to identify molecules that interact with each other and for identifying molecules that can disrupt the interaction between two molecules.

General Methodology

The methods of the present invention utilize prokaryotic host cells to determine and analyze interactions between two molecules and to identify molecules or modifications to molecules that can disrupt such interactions. The methods use a reporter vector that allows for both selection and counterselection with one or more, e.g., two, three, four, or five, reporter genes. The selection and counterselection genes can be part of the same reporter vector or on separate vectors. If the genes are on separate vectors, the vectors may be part of the same DNA molecule or on separate molecules. A DNA binding site can be inserted upstream of the reporter gene(s) in the reporter vector. Alternatively, a library of randomized nucleotides can be cloned upstream of the reporter gene(s) to create a reporter vector library.

DNA binding protein expression vectors are also introduced into the host cells. These constructs encode DNA binding proteins (including proteins being tested for their ability to bind to DNA, e.g., to a particular DNA sequence) and a polypeptide. The constructs can be in the format of a library of molecules (e.g., cDNAs) that are introduced into the cells. Molecules that bind to the DNA sequence can then be isolated using selection and/or counterselection, and identified. Alternatively, a molecule of interest, such as a specific transcription factor, encoded in a DNA binding protein expression vector, can be introduced into host cells into which a reporter vector library has been introduced. DNA sequences bound by the molecule of interest can then be isolated using selection and/or counterselection, and identified. A group of isolated DNA sequences that are bound by the molecule of interest can be analyzed computationally to define its DNA-binding specificity (or DNA binding signature).

In another variation, two molecules that are known to interact can be introduced into the host cells, one in the reporter vector, the other in the DNA binding protein expression vector, and test compounds can then be introduced into the system. Using selection and counterselection, compounds that disrupt the interaction between the two molecules can be identified.

Activation protein expression vectors are also used in the new methods. These constructs encode gene activating domains fused to polypeptides. The polypeptides interact with polypeptides encoded by the DNA binding protein expression vectors. If the DNA binding protein encoded by the DNA binding protein expression vector interacts with the DNA sequence on the reporter vector, it will recruit the gene activating domain to the site and promote transcription of the reporter gene, allowing for selection and/or counterselection.

The DNA binding protein expression vector and the activation protein expression vector can be part of the same chimeric gene; alternatively, they can be encoded by separate chimeric genes.

Reporter Genes

Reporter genes encode gene products that give rise to a detectable signal, e.g., color, fluorescence, luminescence, a cell surface tag, cell viability, relief of a cell nutritional requirement, cell growth, or drug resistance. Reporter genes can be, e.g., amino acid biosynthetic genes, such as a yeast LEU2, HIS3, LYS2, or TRP1 gene, or a bacterial hisB gene; nucleic acid biosynthetic genes, such as a yeast URA3, URA5/URA10, or URA6 gene, or a bacterial pyrF, pyrE, or pyrH gene; the bacterial lacZ gene; the bacterial chloramphenicol transacetylase (cat) gene; the bacterial gus gene; and the green fluorescent protein (GFP) gene.

Reporter genes can be "selectable," "counterselectable," or "selectable/counterselectable" reporter genes. A "selectable" reporter gene is a gene that, when expressed in a cell, confers a growth advantage on the cell when the cell is maintained under selective conditions. Specific selection conditions are known in the art. Selectable reporter genes can include LEU2, TRP1, URA3, and HIS3. "Selective conditions" can be specific for individual selectable reporter genes. For cells expressing a LEU2, TRP1, or HIS3 selectable reporter gene, the corresponding selective conditions can be maintenance in medium deficient in the amino acid leucine, tryptophan, or histidine, respectively. HIS3 can serve as a selectable marker in a strain in which hisB has been deleted and if the cells are grown in the absence of histidine. For cells expressing a URA3 reporter gene, the selective conditions can be maintenance in medium deficient in uracil. Thus, a cell that expresses a selectable reporter gene can be identified by its growth in selective conditions.

Reporter genes can be "counterselectable" reporter genes. A "counterselectable" reporter gene is a gene that, when expressed in a cell, confers a growth disadvantage on the cell when the cell is maintained under counterselective conditions. Counterselectable reporter genes can include URA3, LYS2, GAL1, CYH2, CAN1, ccdB, and sacB. "Counterselective conditions" can be specific for individual counterselectable reporter genes. For cells expressing the URA3, LYS2, CAN1, CYH2, or sacB counterselectable reporter gene, counterselective conditions can be maintenance in medium containing 5-fluoro-orotic acid (5-FOA), medium containing α-aminoadipate, medium lacking arginine and containing canavanine, medium containing cyclohexamide, and medium containing sucrose, respectively. Thus, a cell expressing a counterselectable reporter gene can be identified by the inhibition of its growth under counterselective conditions.

Reporter genes can be "selectable/counterselectable" reporter genes. A "selectable/counterselectable" reporter gene is a reporter gene that, when expressed in a cell, confers a growth advantage on the cell when the cell is maintained under selectable conditions, and confers a growth disadvantage on the cell when the cell is maintained under counterselective conditions. Thus, a single reporter gene can be both a selectable reporter gene and a counterselectable reporter gene. Selectable/counterselectable reporter genes can include URA3, LYS2, and GAL1. In the methods described herein, when both a selectable reporter gene and a counterselectable reporter gene are used, a single selectable/counterselectable reporter gene can be used in lieu of the individual selectable and counterselectable reporter genes. In some embodiments, the URA3 reporter gene can be used as a selectable/counterselectable reporter gene; selective conditions can be maintenance in medium lacking uracil, e.g., medium lacking uracil and containing 6-azauracil (6AU), and counterselective conditions can be maintenance in medium containing 5-FOA.

URA3 is one of the genes involved in uracil biosynthesis. The URA3 gene product is the enzyme orotidine-5'-phosphate decarboxylase. This enzyme functions in the last step of uracil biosynthesis. The URA3 gene product (along with other members of the of the uracil biosynthesis pathway) can convert 5-FOA into 5-fluoro UMP, a suicide substrate for thymidylate synthase. Cells expressing a functional URA3 gene and maintained in 5-FOA will generate the toxic product 5-fluoro UMP, leading to cell death.

6-azauracil (6AU) is metabolized into 6-azauridine 5' phosphate, a competitive inhibitor of the URA3 gene (Levine et al. (1980) Biochem., 19:4993-4999; Losson et al. (1981) Mol. Gen. Genet., 184:394-399). Because 6AU is a competitive inhibitor, its ability to inhibit the URA3 step in uracil biosynthesis is a function of both the concentration of 6AU in the media and of the expression level of URA3. Although it is theoretically possible to tune the sensitivity of a yeast strain expressing a given amount of URA3 to 5-FOA by increasing the concentration of 6AU in the medium, in practice this has proven to be challenging (Vidal et al. (1996) Proc. Natl. Acad. Sci. USA, 93:10315-10320).

In addition to blocking synthesis of UTP, 6AU also blocks the synthesis of GTP (Exinger et al. (1992) Curr. Genet., 22:9-11). In yeast, the reduction of both the UTP and GTP pools can lead to transcriptional arrest of RNA polymerase II (Lee et al. (2001) Mol. Cell Biol., 21:8651-8656; Nakanishi et al. (1995) J. Biol. Chem., 270: 8991-8995; Shimoaraiso et al. (2000) J. Biol. Chem., 275:29623-29627). In contrast, prokaryotes lack RNA polymerase II. In the methods described herein, 6AU can be used as a more effective, e.g., less toxic, reagent for modulating the activity of the URA3 in bacteria than 5-FOA.

6AU can be used in conjunction with any of the methods described herein, or in other known methods employing selectable systems in bacteria. The concentration of 6AU used in the methods described herein can be less than about 100 µg/ml, between about 0.1 µg/ml and about 50 µg/ml, between about 0.2 µg/ml and about 25 µg/ml, e.g., between about 0.3 µg/ml and about 10 µg/ml, or between about 0.4 µg/ml and about 5 µg/ml, e.g., between about 0.5 µg/ml and about 1 µg/ml.

Reporter Vectors

The methods and compositions described herein employ reporter vectors to express reporter genes in prokaryotic cells. As used in the methods and compositions described herein, a "reporter vector" is a nucleic acid that contains a reporter gene that is operably linked to one or more transcriptional regulatory sequences. Transcription of the reporter gene is controlled by the regulatory sequences. The transcriptional regulatory sequences can include a promoter and other regulatory regions that modulate the activity of the promoter, or regulatory sequences that modulate the activity or efficiency of an RNA polymerase that recognizes the promoter. Such sequences are referred to herein collectively as transcriptional regulatory elements or sequences. A promoter that is operably linked to a reporter gene within a reporter vector can be the naturally-occurring promoter for the reporter gene, or the reporter gene can be engineered to be operably linked to a promoter other than the one to which it is naturally operably linked. Examples of suitable promoters include the trp promoter (Nicholset et al. (1983) Meth. Enzymol., 101:155-164), the lac promoter (Casadaban et al. (1980) J. Bacteriol., 143:971-980), and phage gamma promoter system (Queen (1983) J. Mol. Appl. Genet., 2:1-10).

Reporter vectors can be engineered to include a selectable reporter gene, a counterselectable reporter gene, or a selectable/counterselectable reporter gene. The selectable and counterselectable genes can be on the same reporter vector or on separate reporter vectors. If the genes are on separate reporter vectors, the reporter vectors may be part of the same test DNA molecule or can be present on different DNA molecules. A bicistronic reporter vector can be generated that includes both a selectable and a counterselectable reporter gene. The selectable reporter gene can be upstream of the counterselectable reporter gene, or the counterselectable reporter gene can be upstream of the selectable reporter gene. The selectable and counterselectable reporter genes can be operably linked to a single promoter, e.g., a lac promoter. Upstream of the promoter, e.g., a lac promoter, is a DNA binding site. Each reporter gene, once transcribed, is under the control of a separate translational element (Shine-Dalgarno sequence) that regulates the efficiency of protein synthesis. Reporter vectors can be polycistronic reporter vectors and can include one or more, e.g., two or more, reporter genes. Polycistronic reporter vectors can include combinations of selectable, counterselectable, and selectable/counterselectable reporter genes. Reporter vectors containing multiple reporter genes, e.g., three, four, or five reporter genes, can be a single fusion product or a polycistronic system. Alternatively, each reporter vector can include one reporter gene, as long as each of the vectors also includes the same DNA binding site.

Reporter vectors also contain a DNA binding site. By "DNA binding site" is meant a nucleotide sequence that is necessary and sufficient to specifically interact with a polypeptide, such as a DNA binding domain. The DNA binding site is located sufficiently proximal to the promoter sequence of the reporter gene so as to cause increased reporter gene expression upon recruitment of an RNA polymerase complex by the binding of a DNA binding domain. Reporter vectors can include a DNA binding site known to interact with a specific DNA binding domain, e.g., the DNA binding domain of a protein such as a transcription factor. Alternatively, a library of reporter vectors can be generated using molecular biology techniques in which the DNA binding site is varied, for example, engineered to contain a specific variation is intentionally or randomly varied. A library of reporter vectors can be used to identify a DNA binding site that interacts with a specific DNA binding domain, for example, the DNA binding domain of a protein, such as a transcription factor. A DNA binding site can include a nucleotide sequence that is 5 kb, 4 kb, 3 kb, 2 kb, 1 kb, 500 bp, 400 bp, 300 bp, 200 bp, 100 bp, 50 bp, 40 bp, 30 bp, 20 bp, 10 bp, or 5 bp.

The methods described herein include determining the expression of reporter genes, e.g., counterselectable reporter genes, in prokaryotic host cells, generally bacterial cells. Methods known in the art can be used to transform a host cell and expressing a foreign gene in a host cell. Reporter vectors can include plasmids useful for transforming bacteria, e.g., pBR322 (Bolivar et al. (1997) Gene, 2:95-113), a pUC plasmid (Messing (1983) Meth. Enzymol., 101:20-77), pCQV2 (Queen (1983) J. Mol. Appl. Genet., 2:1-10), a pACYC plasmid (Chang and Cohen (1978) J. Bacteriol., 134:1141-1156), a pRW plasmid (Lodge et al. (1992) FEMS Microbiol. Lett., 95:271-276), a pSC101 plasmid (Lutz and Bujard (1997) Nucl. Acids Res., 25:1203-1210), or derivatives thereof.

Reporter vectors can also include selectable markers. By "selectable marker" is meant a gene, the expression of which can be used to select prokaryotic host cells that have been transformed with a construct described herein, e.g., a reporter gene construct, a DNA binding protein expression vector, or an activation protein expression vector. Selectable markers can include antibiotic resistance genes that confer resistance to, e.g., β-lactams, kanamycin, zeocin, chloramphenicol, streptomycin, tetracycline, or gentamycin, operably linked to a promoter. In some embodiments, a promoter that is operably linked to a selectable marker does not contain a nucleotide sequence that is functionally identical to a DNA binding site contained within the promoter of a reporter gene. In some embodiments, a reporter vector does not include a selectable marker and a reporter vector and a plasmid containing a selectable marker can be introduced into a prokaryotic host cell in combination.

Reporter vectors can also contain origins of replication, e.g., a phage f1 origin, a pSC101 origin, a pSC101* origin, a p15A origin, a Col E1 origin, or an F' origin.

DNA Binding Protein Expression Vectors

In the methods described herein, a DNA binding protein expression vector is used to express DNA binding fusion proteins in prokaryotes. As used herein, a "DNA binding protein expression vector" is a nucleic acid that encodes a DNA binding protein, e.g., a fusion protein. As used herein, a "DNA binding fusion protein" is a fusion protein that includes a polypeptide fused to a DNA binding domain. A "DNA binding domain" is a polypeptide, or combination of polypeptides, that can directly interact with a DNA binding site of a reporter vector described herein. The term also includes proteins that are being tested for their ability to bind to a DNA sequence present in a reporter vector. The term "domain" is not meant to be limited to a discrete folding domain. Rather, consideration of a polypeptide as a DNA binding domain can be made by the observation that the polypeptide has a specific DNA binding activity. A DNA binding domain can be derived, e.g., from naturally occurring polypeptides or from artificial sequences, or can be synthesized or engineered. A DNA binding domain can be a single polypeptide or can be formed by a combination of two or more polypeptides as, e.g., homodimers, heterodimers, or heterotrimers.

In some embodiments, a nucleic acid sequence encoding a protein of interest, or a polypeptide library, is cloned in-frame to a nucleic acid sequence encoding a DNA binding domain. A specific DNA binding fusion protein between a polypeptide and a DNA binding domain can be generated using routine techniques. Examples of DNA binding domains that can be used include polypeptides derived from naturally occurring DNA binding proteins and polypeptides derived from proteins artificially engineered to interact with specific DNA sequences. In general, a DNA binding fusion protein causes little or no transcriptional activation of a reporter gene in the absence of an interacting activating fusion protein as described herein. In most cases, a polypeptide fused to a DNA binding domain in a DNA binding fusion protein does not affect the ability of the DNA binding domain to bind to its cognate DNA binding site in a reporter vector.

In some embodiments, the DNA binding domain can be all or a portion of a transcriptional regulatory protein that retains the ability to selectively bind to a particular nucleotide sequence. The DNA binding activity can be provided by using all or a portion of the transcriptional regulatory protein. In some embodiments, amino acids of the DNA binding domain can be mutated to reduce activation of a reporter gene, e.g., a counterselectable reporter gene, transcription in the absence of the binding of an activating fusion protein described herein.

The DNA binding domain used in the methods described herein can be any DNA binding domain known in the art. Examples of such DNA binding domains include the LysR family of transcriptional regulators, e.g., Trp1, HvY, OccR, OxyR, CatR, NahR, MetR, CysB, NodD, or SyrM (Schell (1993) Ann. Rev. Microbiol., 47:597-626); the DNA binding portions of a PhoB/OmpR-related protein, e.g., PhoB, OmpR, CacC, PhoM, PhoP, ToxR, VirG, or SfrA (Makino et al. (1996) J. Mol. Biol., 259:15-26); the DNA binding portions of histones H1 or H5 (Suzuki and Brenner (1995) FEBS Lett., 372:215-221); the DNA binding portions of a P22 Arc repressor, such as MetJ, CENP-B, Rap1, Xy1S/Ada/AraC, Bir5, or DtxR; the DNA binding domain from proteins of eukaryotic origin, such as Zif268, p53, Jun, Fos, GCN4, or GAL4; or the DNA binding domain from a viral protein, e.g., a papillomavirus E2 protein. The DNA binding domain can be one that is not naturally occurring and can be generated by combinatorial mutagenic techniques such as those described in U.S. Pat. No. 5,198,346. Alternatively, the DNA binding domain can be a molecule that is not known to bind to DNA, but is being screened for its ability to bind to DNA; for example, it is a member of a library being assayed for the presence of DNA binding molecules.

A DNA binding fusion protein can include any protein of interest, or portion thereof, including a protein or portion or fragment thereof, that is of unknown, known, or suspected diagnostic, therapeutic, or pharmacological significance. Such a protein can be, e.g., an oncoprotein such as Myc, Ras, Src, and Fos; a tumor-suppressor protein such as p53, Rb, an INK protein such as p16INK4a and p15INK4b, and CIP/KIP proteins, e.g., p21CIP1 and p27KIP1; other proteins involved in cell-cell regulation including kinases and phosphatases; proteins or portions thereof involved in signal transduction (e.g., domains such as SH2, SH3, ITAMs, ITIMs, kinase, phospholipase, or phosphatase domains) and cytoplasmic tails of receptors; cytoskeletal proteins; or viral proteins.

A DNA binding protein expression vector can be generated using known techniques in molecular biology, e.g., recombinant DNA techniques. The joining of various DNA fragments coding for different polypeptide sequences can be performed by employing, e.g., blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. The DNA binding protein expression vector can be synthesized using known techniques, including automated DNA synthesizers. In some embodiments, PCR amplification of gene fragments can be carried out using anchor DNA primers that give rise to complementary overhangs between two consecutive gene fragments that can subsequently be annealed to generate a chimeric gene sequence (e.g., *Current Protocols in Molecular Biology*, Eds. Ausubel et al. John Wiley & Sons: 1992). Other recombination methods can include the GATEWAY® cloning technique (Invitrogen).

Activation Protein Expression Vectors

In the methods described herein, activation protein expression vectors are used to express activating fusion proteins in prokaryotes. As used herein, an "activation protein expression vector" is a nucleic acid that encodes an activating fusion protein. As used herein, an "activating fusion protein" is a fusion protein that includes a polypeptide fused to a gene activating domain. A "gene activating domain" is a polypeptide that can induce the expression of a gene, e.g., a reporter gene such as a counterselectable reporter gene, to whose control region (e.g., promoter) it is directly or indirectly associated with.

In some embodiments, the activating fusion protein includes a prey polypeptide capable of forming an intermolecular association with a bait polypeptide that is to be tested for binding activity, and also includes a gene activating domain. A gene activating domain can include, e.g., all or a portion of an RNA polymerase subunit, such as the polymerase interaction domain of the N-terminal domain ($\alpha$-NTD) of the RNA polymerase a subunit (Dove et al. (1997) Nature, 386:627-6390; Dove and Hochschild (1998) Genes Dev., 12:745-754). A protein-protein interaction between a bait polypeptide and a prey polypeptide can link the DNA binding domain of the DNA binding fusion protein with the gene activating domain of the activating fusion protein, generating a protein complex that can directly recruit a functional RNA polymerase enzyme to DNA sequences proximate to the DNA binding site, e.g., to the reporter gene, e.g., a counterselectable reporter gene. The RNA polymerase can be an endogenous prokaryotic RNA polymerase or can be an exogenous RNA polymerase, e.g., a bacteriophage T7 RNA polymerase.

DNA dependent RNA polymerase in *E. coli* and other bacteria consists of an enzymatic core composed of subunits $\alpha$, $\beta$, and $\beta'$ in the stoichiometry $\alpha_2\beta\beta'$, and one of several alternative factors responsible for specific promoter recognition. In some embodiments, the activating fusion protein includes a sufficient portion of the amino-terminal domain of the $\alpha$ subunit to permit assembly of transcriptionally active RNA polymerase complexes that include the activating fusion protein. The $\alpha$ subunit, which initiates the assembly of RNA polymerase by forming a dimer, has two independently folded domains (Ebright and Busby (1995) Curr. Opin. Genet. Dev., 5:197-203). The larger amino-terminal domain ($\alpha$-NTD) mediates dimerization and the subsequent assembly of the polymerase complex. A prey polypeptide can be fused in frame to the $\alpha$-NTD, or a fragment thereof that retains the ability to assemble a functional RNA polymerase complex.

In some embodiments, a functional gene activating domain can be generated by two activation protein expression vectors. A first activation protein expression vector can include a nucleic acid sequence encoding a prey polypeptide cloned in-frame to a sequence encoding a first partial gene activating domain, e.g., a portion of the yeast protein $GAL11^P$, a mutant form of GAL11 (Himmelfarb et al. (1990) Cell, 63:1299-1309). The "P" mutation confers upon GAL11, a component of the RNA polymerase II holoenzyme in yeast, the ability to interact with the dimerization domain of GAL4. A second activation protein expression vector can include a nucleic acid sequence encoding a second partial gene activating domain, e.g., GAL4, cloned in-frame to a sequence encoding a sufficient portion of the amino-terminal domain of the $\alpha$ subunit. In the methods described herein, the two activation protein expression vectors can be co-expressed in a host cell to activate the expression of a reporter gene, e.g., a counterselectable reporter gene.

The methods described herein can include the use of "polymerase interaction domains" which are defined as proteins containing portions of other RNA polymerase subunits or portions of molecules that associate with an RNA polymerase subunit or subunits. In some embodiments, the activating fusion protein can include a gene activating domain of a transcriptional activator protein. The DNA binding fusion protein, by forming DNA complexes with the activating fusion protein, can indirectly recruit RNA polymerase complexes to the promoter sequences of the reporter gene, e.g., a counterselectable reporter gene, thus activating transcription of the reporter gene, e.g., a counterselectable reporter gene. The gene activating domain can be derived from, e.g., PhoB or OmpR.

The activating fusion proteins can differ in the prey polypeptides they include. A prey polypeptide can be derived, e.g., from all or a portion of a known protein or a mutant thereof, all or a portion of an unknown protein, e.g., a protein encoded by a gene cloned from a cDNA library, a random polypeptide sequence, or a random polypeptide sequence included in a larger polypeptide sequence. The methods described herein can isolate DNA sequences encoding novel interacting proteins by fusing members of a DNA expression library, e.g., a cDNA or synthetic DNA library, e.g., a random or intentionally biased DNA library, in-frame to a gene activating domain to generate a library of activating fusion proteins. The library-encoded proteins that physically interact with the promoter-bound DNA binding fusion protein can detectably alter expression of a reporter gene, e.g., a counterselectable reporter gene, and can provide a ready assay for identifying a particular DNA clone encoding an interacting protein of interest. A library described herein can be cloned into either a DNA binding fusion protein or an activating fusion protein.

In some embodiments, an activation protein expression vector can be generated to encode a prey protein, e.g., a transcription factor, or fragment thereof, that contains an endogenous DNA binding domain, and the activation protein expression vector can be used without a DNA binding domain in the methods described herein. Such proteins that can be used in the methods described herein can be, e.g., transcription factors, e.g., Zif268, TerR, Arc repressor, p53, GCN4, c-Fos, c-Jun, AP-1, HSF, GR, Engrailed, NF-AT, Lef-1, or synthetic transcription factors.

Prokaryotic Host Cells

Prokaryotic host cells can be used in the methods described herein. Prokaryotic host cells can include, e.g., bacterial strains of *Escherichia*, such as *Escherichia coli*; *Bacillus* such as *Bacillus subtilis*; *Streptomyces*; *Pseudomonas*; *Salmonella*; *Serratia*; and *Shigella*. The choice of an appropriate host cell, e.g., bacterial host cell, can be influenced by the choice of a reporter gene, e.g., a counterselectable reporter gene.

In some embodiments, a host cell, e.g., a bacterial host cell, lacks a functional endogenous gene corresponding to the reporter gene. For example, the cell may lack a counterselectable gene that corresponds to the reporter gene. Thus, in one example, the host cell may lack a functional endogenous pyrF gene when an exogenously-derived pyrF or URA3 gene is used as a counterselectable reporter. Or a non-functional endogenous hisB gene may be present when a hisB or his3gene is the selectable reporter gene. In some embodiments, a host cell can lack a functional endogenous gene, e.g., a pyrF gene, and can be transformed with a reporter vector that contains a functional homologous reporter gene, e.g., a eukaryotic URA3 gene. The endogenous reporter genes and the reporter genes in a reporter vector can be any of the reporter genes described herein, e.g., a counterselectable reporter gene, a selectable reporter gene, or a selectable/counterselectable reporter gene.

A bacterial host cell can lack multiple functional endogenous genes, e.g., a functional selectable reporter gene (e.g., a hisB gene) and a functional counterselectable reporter gene (e.g., a pyrF gene). A bacterial host cell lacking multiple functional endogenous genes can be transformed with a reporter vector, e.g., a bicistronic reporter vector or a polycistronic reporter vector, and can be used, for example, in methods employing sequential selection under selective and counterselective conditions.

Prokaryotic host cells can be maintained using routine culture methods and the host cells can be transformed with the constructs and vectors or nucleic acid sequences described herein using routine transformation methods.

Methods of Determining DNA/Protein Interactions

The methods described herein can be used to determine the interaction between a DNA molecule and a protein within prokaryotic cells. The interaction between a DNA molecule and a protein can be determined by using constructs described herein, e.g., a reporter vector and an activation protein expression vector. A reporter vector can contain a bait nucleotide sequence and an activation protein expression vector can contain a prey polypeptide.

The new methods can provide high-throughput assays for determining the sequence specificity of a given DNA binding protein (e.g., a transcription factor). For example, the methods can be used to determine the sequence specificity of monomers or homodimers of DNA binding proteins. In some embodiments, a DNA sequence that binds to a known protein can be identified through the use of combinatorial libraries of reporter vectors, e.g., bicistronic reporter vectors. A reporter vector library, e.g., a bicistronic reporter vector library, can be constructed by inserting random bait DNA binding sites into a reporter vector, e.g., a bicistronic reporter vector. An activation protein expression vector containing a nucleotide sequence encoding a known bait polypeptide, e.g., a transcription factor, in frame to a nucleic acid sequence encoding a gene activating domain can be generated, and the prey reporter vector library, e.g., the prey bicistronic reporter vector library, and bait activation protein expression vectors can be transformed into prokaryotic host cells. The host cells can then be assayed for reporter gene expression as described herein. Host cells expressing a reporter gene can be isolated, the reporter vectors, e.g., the bicistronic reporter vectors, can be isolated from the host cells, and the DNA sequences of the prey DNA binding site can be determined.

The selection of DNA binding signatures within a library can be accomplished using various procedures, including a procedure known as Systematic Evolution of Ligands by Exponential Enrichment or "SELEX." The SELEX method is described in, e.g., Gold et al., U.S. Pat. Nos. 5,270,163 and 5,567,588; Fitzwater et al. (1996) Methods Enzymol., 267: 275-301; and Ellington and Szostak (1990) Nature, 346:818-22. Briefly, a heterogeneous DNA oligomer population is synthesized to provide candidate oligomers for the selection of DNA binding sequences (e.g., bait). This initial DNA sequence population can be a set of random sequences 15 to 100 nucleotides in length flanked by fixed 5' and 3' sequences 10 to 50 nucleotides in length. The fixed regions can provide sites for PCR primer hybridization and, in one implementation, for initiation of transcription by an RNA polymerase to produce a population of RNA oligomers. The fixed regions can also contain restriction sites for cloning selected DNA sequences. Many examples of fixed regions can be used in DNA sequence evolution. See, e.g., Conrad et al. (1996) Methods Enzymol., 267:336-83; Ciesiolka et al. (1996) Methods Enzymol., 267:315-35; Fitzwater, supra. Once the population of random sequences is generated, functional molecules, that is nucleic acids that interact with the target polypeptide, can be enriched through a variety of methods, such as capture of polypeptide-nucleic acid complexes on a solid support or electrophoretic mobility shift assay. Following enrichment, the resulting nucleic acid pool is amplified and the process repeated until the remaining nucleic acid population primarily consists of members that interact specifically with the polypeptide.

The DNA binding sites can be sequenced using routine methods, or by using PCR or restriction digests followed by ligation to concatamerize the DNA binding sites before sequencing (Roulet et al. (2002) Nat. Biotech., 20:831-835). The DNA sequences can be further analyzed using sequence alignment algorithms, e.g., MEME, CONSENSUS (Hertz et al. (1990) Comput. Appl. Biosci., 6:81-92), YEBIS (Yada et al. (1998) Bioinformatics, 14:317-325), ANN Spec (Workman et al. (2000) Pac. Symp. Biocomput., 468-478), or Scanseq (Papatsenko et al. (2002) Genome Res., 12:470-481), to determine a consensus DNA binding motif for a bait polypeptide.

In some embodiments, the methods described herein can be used to identify a protein that can bind to a known DNA sequence through the use of combinatorial libraries of prey activation protein expression vectors. A prey activation protein expression vector library can be constructed by inserting nucleotide sequences encoding random prey polypeptides into an activation protein expression vector in-frame with a gene activating domain. The library can then be transformed into prokaryotic host cells to produce a large number of prey activating fusion proteins. The host cells can also be transformed with a bait reporter vector and assayed for reporter gene expression as described herein. Host cells expressing a reporter gene can be isolated, the prey activation protein expression vectors can be isolated from the cells, and the polypeptide sequence encoded by the prey activation protein expression vector can be determined.

In some embodiments, the methods described herein can be used to identify a test compound that inhibits or is capable of inhibiting the interaction of a DNA sequence and a protein. In some embodiments, the reporter vector contains a counterselectable reporter gene, and the ability of a test compound to interfere with the interaction of a DNA molecule and a protein can be assayed by measuring cell growth in counterselective conditions described herein. In some embodiments, the counterselectable reporter gene is a URA3 reporter gene, and the counterselective conditions include maintenance in medium containing uracil and 5-FOA. Host cells, e.g., bacterial cells lacking a functional pyrF gene, are transformed with a reporter vector containing a bait DNA binding site and with a prey activation protein expression vector containing a nucleotide sequence encoding a prey polypeptide capable of binding to the bait DNA binding site.

When the host cells are maintained under counterselective conditions, e.g., in medium containing uracil and 5-FOA, the interaction of the prey activating fusion protein and the bait DNA binding site causes the expression of the reporter gene, e.g., the counterselectable reporter gene, e.g., the URA3 gene, and the host cells do not grow. Compounds that disrupt the interaction of the bait DNA binding site and the prey activating fusion protein prevent the expression of the reporter gene, e.g., the counterselectable reporter gene, e.g., the URA3 gene, and the host cells will grow under counterselective conditions, e.g., in medium containing uracil and 5-FOA. The test compound can be expressed within the host cell using routine methods for gene expression, or the test compound can be added directly to the medium. A test compound can be, e.g., a polypeptide, a nucleic acid, or a small, organic molecule, e.g., a molecule having a molecular weight of less than 1 kD.

The methods can be used to identify protein modifications, e.g., phosphorylation or acetylation, that can affect DNA-protein interactions. The methods described can also be used to determine the interaction between a protein and a modified DNA molecule, e.g., a methylated DNA molecule, by determining the binding in the presence or absence of a DNA methyltransferase. Methods of introducing such enzymes are known in the art. Thus, an advantage of a counterselectable system is the ability to identify compounds or modifications that block the interaction between two molecules, e.g., a DNA molecule and a protein.

Methods of Determining Protein/Protein Interactions

The methods described herein can be used to determine the interaction between two proteins. For example, the new methods can be used to identify proteins that bind to other proteins, to determine amino acids that mediate the interaction, and to identify compounds or polypeptides capable of disrupting the interaction. The methods can also be used to identify protein modifications, e.g., phosphorylation, methylation, or acetylation, that can affect protein interactions.

In some embodiments, the methods described herein can be used to identify a protein that binds to another protein using a reporter vector, a bait DNA binding protein expression vector, and a prey activation protein expression vector described herein. A reporter vector can be engineered to include a DNA binding site specific for a DNA binding domain. A bait DNA binding protein expression vector can be generated to include a nucleotide sequence encoding a fusion protein that includes a DNA binding domain and a test protein, e.g., a bait polypeptide. A prey activation domain can be generated to include a nucleotide sequence encoding a prey activating fusion protein that includes a second test protein, e.g., a prey polypeptide, and a gene activating domain. The three constructs are transformed into a prokaryotic host cell, and the host cell can be assayed for expression of the reporter gene as an indication that the two proteins interact.

In some embodiments, the methods described herein can be used to identify a protein that can bind to a known protein through the use of combinatorial libraries of DNA binding protein expression vectors. A prey DNA binding protein expression vector library can be constructed by inserting nucleotide sequences encoding random prey polypeptides into a DNA binding protein expression vector in-frame with a DNA binding domain. The prey DNA binding protein expression vector library and a bait activation protein expression vector encoding a known bait polypeptide can then be transformed into host cells.

In some embodiments, a prey activating construct library can be constructed by inserting nucleotide sequences encoding random prey polypeptides into an activation protein expression vector in-frame with a gene activating domain. The prey activation protein expression vector library and a bait DNA binding protein expression vector encoding a known bait polypeptide can then be transformed into prokaryotic host cells.

In some embodiments, a bait DNA binding protein expression vector library and a prey activation protein expression vector library can be constructed and transformed into host cells. The host cells can be assayed for expression of the reporter gene as an indication of protein-protein interaction. The bait DNA binding protein expression vectors and the prey activation protein expression vectors can be isolated and the bait polypeptides and the prey polypeptides encoded by the constructs can be determined.

In other embodiments, the methods described herein can be coupled with methods for mutagenizing proteins to identify amino acid residues responsible for the interaction of proteins. For example, mutations in one or both of two proteins that prevent the two proteins from interacting indicate that amino acids at those positions contribute to the ability of the wild-type proteins to interact. Similarly, compensatory mutations in two interacting proteins define critical amino acids that contribute to the ability of the corresponding wild-type proteins to interact. The mutations can be specifically engineered or the mutations can be randomly engineered.

In other embodiments, the methods described herein can be used to identify test compounds that disrupt the interaction of two proteins. The test compounds can be introduced as described herein, and the reporter gene can be a counterselectable reporter gene to identify a compound that disrupts protein-protein interactions as one that allows host cells to grow under counterselective conditions described herein.

In other embodiments, a compound that disrupts protein-protein interactions can be identified using a reporter vector that includes both a selectable reporter gene and a counterselectable reporter gene. A host cell transformed with a reporter vector, a bait DNA binding protein expression vector, and a prey activation protein expression vector can first be maintained under selective conditions in the absence of a test compound, and host cells that grow can be identified as cells that express two interacting proteins. Host cells can then be grown under counterselective conditions in the presence of a test compound and host cells that survive can be used to identify a test compound that disrupts protein-protein interaction.

Methods of Determining Protein/RNA Interactions

The methods described herein can be used to determine the interaction between a protein and an RNA molecule. In some embodiments, a reporter vector and a prey activation protein expression vector, containing a test protein, e.g., a prey polypeptide, are generated. A "DNA/RNA binding construct" is engineered that contains a nucleotide sequence encoding a DNA/RNA binding fusion protein. A "DNA/RNA binding fusion protein" includes a DNA binding domain fused to a non-random RNA binding domain. A "non-random RNA binding domain" is an amino acid sequence that binds to a known non-random RNA sequence. A bait "linker RNA construct" is generated that contains a nucleic acid sequence that is transcribed to generate a bait linker RNA molecule. A bait "linker RNA molecule" is an RNA molecule that includes a known non-random RNA sequence fused to a test RNA molecule, e.g., a bait RNA molecule. The known non-random RNA sequence specifically binds to the non-random RNA binding domain of the DNA/RNA binding fusion protein. The reporter vector, the DNA/RNA binding construct, the bait linker RNA construct, and the prey activation protein expression vector are all transformed into a prokaryotic host cell. The interaction of the prey polypeptide and the bait RNA molecule can be identified by the expression of the reporter gene. The use of libraries described herein and the identification of test compounds that disrupt the interactions described herein can also be used.

Methods of Determining RNA/RNA Interactions

The methods described herein can be used to determine the interaction between two RNA molecules. In some embodiments, a reporter vector is first generated. A DNA/RNA binding construct is engineered that includes a nucleotide sequence encoding a DNA/RNA binding fusion protein containing a DNA binding domain and a first known non-random RNA binding domain. A "bait linker RNA construct" is generated that contains a nucleic acid sequence that is transcribed to generate a bait linker RNA molecule. A "bait linker RNA molecule" is an RNA molecule that includes a first known non-random RNA sequence fused to a first test RNA molecule, e.g., a bait RNA molecule. The first non-random RNA sequence specifically binds to the first non-random RNA binding domain of the DNA/RNA binding fusion protein. A "prey linker RNA construct" is engineered that contains a nucleic acid sequence that is transcribed to generate a prey linker RNA molecule. A "prey linker RNA molecule" is an RNA molecule that includes a second test RNA molecule, e.g., a prey RNA molecule, fused to a second known non-random RNA sequence. An "RNA activation protein expression vector" is generated that includes a nucleotide sequence encoding an RNA binding/activating fusion protein. An "RNA binding/activating fusion protein" is a fusion protein that contains a second known non-random DNA binding domain fused to a gene activating domain. The second known non-random DNA binding domain specifically binds to the second known non-random sequence of the prey linker RNA construct. The interaction of the bait RNA molecule and the prey RNA molecule can be identified by the expression of the reporter gene. The use of libraries described herein and the identification of test compounds that disrupt the interactions described herein can also be used.

Rarified Libraries

One of the key advances provided by the availability of a counterselectable marker is the ability to apply a second "test" to any molecules that are selected using a positive selectable marker. One inherent problem with the use of a positive selectable marker is the ability of a fraction of the host cells to survive the selection by upregulation of the reporter gene in a manner that is independent of the desired bait-prey interaction. This could be due to an inherent property of a library of nucleic acid sequences that are introduced upstream of the promoter, or through mutational or recombination of the promoter driving the reporter genes. The counterselectable marker provides a second test for surviving clones: In the absence (or by inactivation) of the bait, true positive clones (prey) will no longer activate the reporter genes and these cells will survive counterselection whereas false positive clones that have upregulated expression of the reporter genes independent of the bait-prey interaction will be eliminated under these conditions. In principle, the order of the positive and negative selection steps can be reversed (see below).

A two-step selection procedure (i.e., positive selection followed by negative selection) in bacteria can successfully determine the sequence specificity of a prey molecule (e.g., DNA-binding domain). After the first positive selection step, a negative selection step (e.g., counterselection with 5-FOA) is often required because false positive prey (e.g., a prey DNA sequence that on its own, i.e., in the absence of the bait, can activate the promoter) may exist in the system. A problem with these false positives is that they may preclude the identification of interacting bait and prey molecules (true positives) if the false positive prey are present at a level that significantly exceeds the number of true positives. The efficiency of the selections could be improved if all false positive prey were first eliminated by negative selection before introducing a prey molecule into cells.

A rarified library is one in which false positive prey have been eliminated from the library by negative selection. To generate a rarified library, the order of the positive and negative selections is inverted. By performing the negative selection first, the library can be purged of the majority of the false positive clones before it is used in the presence of a bait molecule (e.g., a transcription factor bait) to isolate prey (e.g., target DNA binding sites) that are recognized by the bait. Instead of performing two steps of selection (for example, positive selection with 3-AT followed by negative selection with 5-FOA) with every prey molecule (e.g., transcription factor) that is assayed, the negative selection can be performed once to generate a "rarified library" and this library can then be used for all subsequent selections with different baits. This allows their DNA-binding specificity to be determined in a single selection step.

Kits

The methods and compositions described herein can be embodied in a kit for detecting interactions of molecules. A kit can include any of the constructs described herein, e.g., a reporter vector, a DNA binding protein expression vector, an activation protein expression vector, a DNA/RNA binding construct, a linker RNA construct, and an RNA activation protein expression vector. A kit can also include a prokaryotic host cell described herein that lacks an endogenous functional gene, where the reporter gene included in the reporter vector is the same as the endogenous gene. A kit can also include a prokaryotic host cell that lacks an endogenous functional gene, where the reporter gene included in the reporter vector is homologous to the endogenous gene. A kit can also include constructs with known nucleotide sequence insertions and libraries of constructs containing random nucleotide sequences described herein. A kit can also include a library of prokaryotic host cells that contain a library of a construct described herein. A kit can also contain reagents, e.g., selective and counterselective reagents described herein. Additionally, a kit can include instructions for using the kit to practice the methods described herein. The instructions can be in writing in a tangible form or stored as an electronically retrievable form.

In some embodiments, a kit can be used to determine the interaction between a DNA molecule and a protein. The kit can include a reporter vector that contains a DNA binding site and a reporter gene, e.g., a counterselectable reporter gene, e.g., a URA3 gene. The kit also includes an activation protein expression vector that includes a nucleotide sequence that encodes a prey polypeptide fused to a gene activating domain. The reporter vector and the activation protein expression vector can contain libraries described herein. The kit can also include a prokaryotic cell that lacks an endogenous functional gene described herein. The kit can also include reagents, e.g., reagents that allow for selection and/or counterselection, e.g., 6AU, described herein.

In some embodiments, a kit can be used to determine the interaction between two proteins. The kit can include a reporter vector, a DNA binding protein expression vector, and an activation protein expression vector. The reporter vector can contain a reporter gene, e.g., a counterselectable reporter gene, e.g., a URA3 gene. The kit can include prokaryotic host cells lacking an endogenous functional gene described herein, and reagents, e.g., reagents that allow for selection and/or counterselection described herein. The DNA binding protein expression vector and the activation protein expression vector can contain libraries described herein.

A kit for detecting a protein-protein interaction can include two vectors, a host cell, and (optionally) a set of primers for cloning one or more genes encoding test proteins (e.g., from a patient sample). The first vector may contain a promoter, a transcription termination signal, and other transcription and translation signals functionally associated with the first chimeric gene to direct the expression of a first chimeric gene. The first chimeric gene includes a DNA sequence that encodes a DNA-binding domain and a unique restriction site(s) for inserting a DNA sequence encoding either the target (prey) or test polypeptide (bait), or a fragment thereof, in such a manner that the cloned sequence is expressed as part of a hybrid or fusion protein with the DNA-binding domain. The first vector also includes a means for replicating itself (e.g., an origin of replication) in the host cell. The first vector also includes a first, selectable marker gene, the expression of which in the host cell permits selection of cells containing the first marker gene from cells that do not contain the first marker gene. The first vector may optionally also contain a second, counterselectable marker gene as described herein. The first vector can be a plasmid, though it may optionally be genomically integrated where the chimeric gene encodes the target protein.

The kit can also include a second vector that contains a second chimeric gene. The second chimeric gene can also include a promoter and other relevant transcription and translation sequences to direct expression of a second chimeric protein. The second chimeric gene can include a DNA sequence that encodes an "activation tag" and a unique restriction site(s) to insert a DNA sequence encoding either the target (prey) or sample (bait) protein (whichever is not cloned into the first chimeric gene), in such a manner that the cloned protein is capable of being expressed as part of a fusion protein with the activation tag. As appropriate, the second vector can be a plasmid or be genomically integrated. The kit can be provided with one of the two vectors already including the target protein.

In some embodiments, a kit can be used to determine the interaction between a protein and an RNA molecule. The kit can include a reporter vector, a DNA/RNA binding construct, a linker RNA construct, and an activation protein expression vector. The linker RNA construct and the activation protein expression vector can contain libraries described herein. The kit can also include a prokaryotic host cell and reagents that allow for selection and/or counterselection described herein.

In some embodiments, a kit can be used to determine the interaction between two RNA molecules. The kit can include a reporter vector, a DNA/RNA binding construct, a first linker RNA construct, a second linker RNA construct, and an RNA activation protein expression vector. The linker RNA constructs can include libraries described herein. The kit can also include a prokaryotic host cell and reagents that allow for selection and/or counterselection described herein.

EXAMPLES

The invention is further illustrated by the following examples. The examples are provided for illustrative purposes only. They are not to be construed as limiting the scope or content of the invention in any way.

Example 1

Construction of a ΔpyrF Prokaryotic Cell Line

The current design of the bacterial two-hybrid system allows for only positive selection using the HIS3 reporter gene. By substituting the URA3 gene for HIS3 in the reporter system and performing the selection in a bacterial strain with the URA3 homolog (pyrF) inactivated (Broschard et al. (1998) Carcinogenesis, 19:305-310), a negative selection can be performed in medium containing 5-fluoro orotic acid (5-FOA). Proteins can then be selected for their inability to bind a target sequence in the URA3 promoter (one-hybrid) or for the absence of an interaction between two molecules (two-hybrid/or three-hybrid), since lower expression levels of URA3 can provide increased tolerance to 5-FOA (Boeke et al. (1987) Meth. Enzymol., 154:164-175).

To determine the interaction between a DNA molecule and a protein, a prokaryotic cell line lacking a functional endogenous pyrF gene was first constructed. The pyrF gene in bacterial strains KJ1C(Joung et al. (2000) Proc. Natl. Acad. Sci. USA, 97:7382-7387) and US0 was knocked out using the methodology described by Datsenko et al. (2000) Proc. Natl. Acad. Sci. USA, 97:6640-6645. The US0 strain is isogenic to KJ1C except that it lacks the Tn10 insertion conferring tetracycline resistance. Making site-specific insertions or deletions in the bacterial genome using homologous recombination can be performed by methods known in the art. Using this system, the majority of the pyrF gene was deleted, as indicated in FIG. 1A.

Figure 1B:
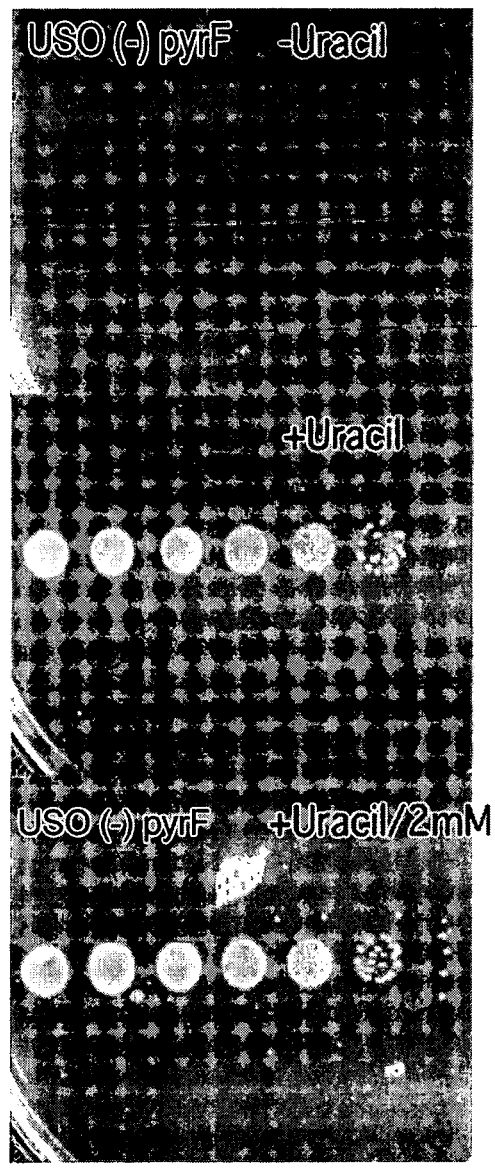
FIG. 1B is a representation of US0(ΔpyrF) cells maintained under various growth conditions.

The new ΔpyrF strains were maintained under various growth conditions (FIG. 1B). The cells were serially diluted ten-fold and the results are illustrated in FIG. 1B from left to right. The ΔpyrF cells grew only in the presence of uracil and were insensitive to 5-FOA. Thus, the ΔpyrF cells were resistant to 5-FOA and required uracil for growth on minimal media (FIG. 1B).

Example 2

Determination of the Interaction Between the Transcription Factor Zif268-cFos and a DNA Binding Site Using a Counterselectable Reporter 5-FOA, in conjunction with ΔpyrF strains, can be used to select against transcription factors that activate a URA3 reporter incorporated into the F' episome. 3-AT (3-amino 1,2,4-triazole) can be used to select for activation of the HIS3 reporter. A URA3 reporter containing a desired transcription factor target site was incorporated into the F' episome by homologous recombination as described in Joung et al. for creating the corresponding HIS3 reporter strains (Joung et al. (2000) Proc. Natl. Acad. Sci. USA 97:7382-7387).

To test the feasibility of using the URA3 reporter system to discriminate between transcription factors that differentially activate a reporter, the survival of two different US0 strains having different target sites incorporated upstream of the URA3 reporter were compared. One US0 strain contained a reporter that included a perfect DNA target sequence (5'-CCCACGCGTGGG-3' (SEQ ID NO:2); "TGG") for the transcription factor Zif268-cFos (Wolfe et al. (2000) Structure 8:739-750), which is known to bind to DNA as a homodimer. The other US0 strain contained a reporter that included a target DNA sequence that differed at 4 of the 12 base pairs (5'-CACCCGCGGGTG-3' (SEQ ID NO:3); "GGT"). Both strains harbored a plasmid encoding the transcription factor Zif268-cFos. The transcription factor Zif268-cFos, when fused to Gal-11P and in the presence of the α-GAL4 fusion protein, is known to significantly activate only the "TGG" reporter (and not the "GGT" reporter) when lacZ is the reporter gene.

Figure 2:
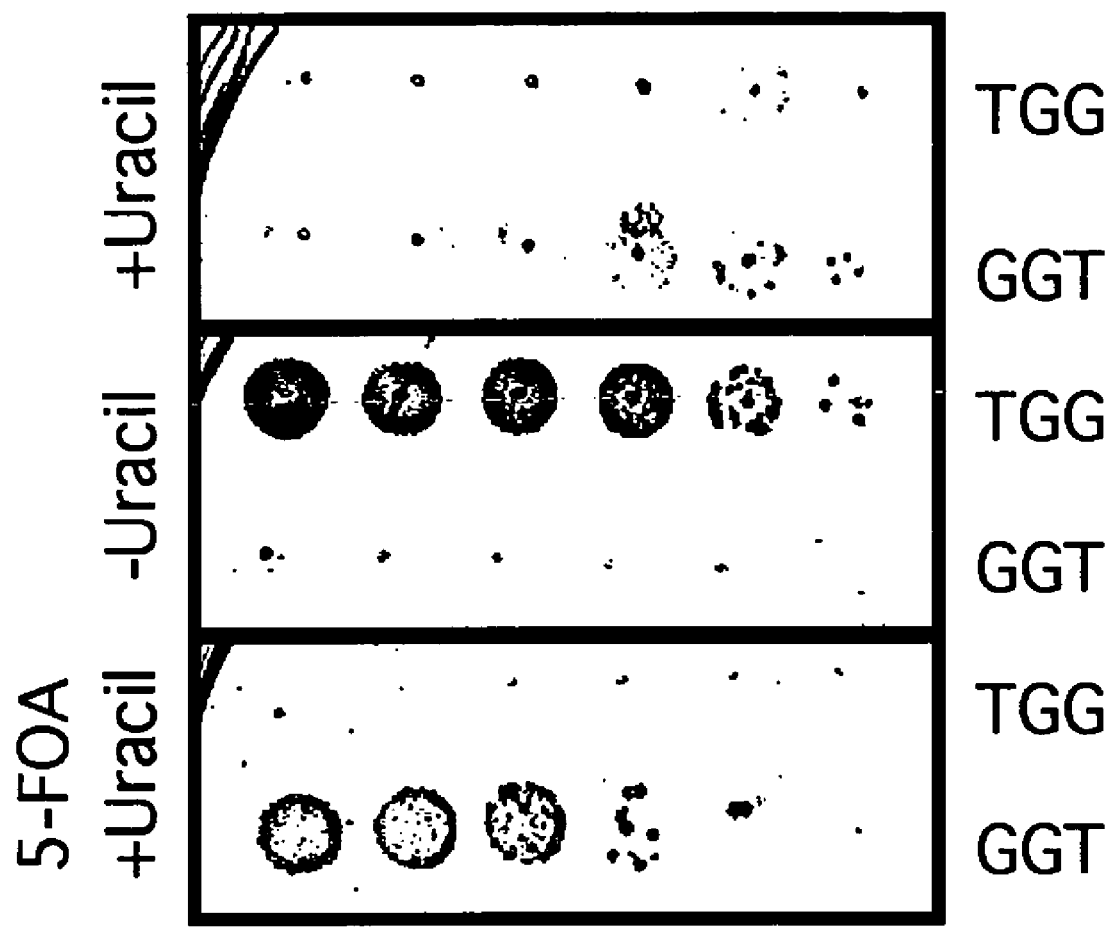
FIG. 2 is a representation of US0(ΔpyrF) cells maintained under various growth conditions with different homodimeric target sites in the promoter ("TGG" or "GGT") of the URA3 reporter gene.

The cells were serially diluted ten-fold. The results of these experiments are illustrated in FIG. 2 from left to right. Both strains grew equally well in the presence of 0.1 mM uracil (FIG. 2). However, when 0.05 mM 5-FOA was added to the media, the "TGG" strain was selectively killed. The "GGT" strain, which contained a mismatched binding site in the URA3 reporter, was insensitive to 5-FOA at this concentration in the presence of the same transcription factor. This demonstrates that a prokaryotic counterselectable reporter system is useful for determining the interaction of a DNA molecule and a protein.

Example 3

Construction of Prokaryotic Host Cells with Increased Sensitivity to 5-FOA

To create a prokaryotic host cell with increased sensitivity to 5-FOA, a URA3 construct that was derived from the *Saccharomyces cerevisiae* URA3 gene-containing plasmid yep24 was used. The URA3 construct was obtained from the yep24 plasmid by PCR, using primers that included appropriate restriction enzyme cleavage sites and a leader sequence to allow translation within bacteria. The URA3 construct was cloned directly into a derivative of $P_{zif}$-HIS3-aadA (Joung et al. (2000) Proc. Natl. Acad. Sci. USA, 97:7382-7387) to replace the HIS3 gene. This placed the URA3 gene under control of a lac promoter (Lanzer et al. (1988) Proc. Natl. Acad. Sci. USA, 85:8973-8977). When this new construct was introduced into the F' episome of US0(ΔpyrF), the basal level of URA3 expression was very low compared to a wild-type US0 strain, as detected by growth on minimal medium lacking uracil. This is illustrated in the limited growth of the "GGT" strain in the "-Uracil" panel in FIG. 2.

It was surmised that the problem with expression might be due to differences in the preferred codon usage between bacteria and yeast. In particular, rare arginine codons, such as AGA and AGG, in conjunction with certain stop codons, can lead to ribosome stalling and protein degradation via the SsrA tagging pathway (Hayes et al. (2002) Proc. Natl. Acad. Sci. USA, 99:3440-3445).

To address this issue, two new versions of the URA3 gene were constructed. First, "construct–TE" was a modified URA3 gene in which the codon usage was altered at the C-terminus and the termination codons to increase translational efficiency (FIG. 3). This construct also included an improved Shine-Dalgarno sequence to enhance translational efficiency (Tan (2001) Protein Expr. Purif., 21:224-234). Second, "construct SD+" was identical to "construct–TE" except that it also included a translational enhancer (Tan, supra) upstream of the modified URA3 gene.

Figure 4:
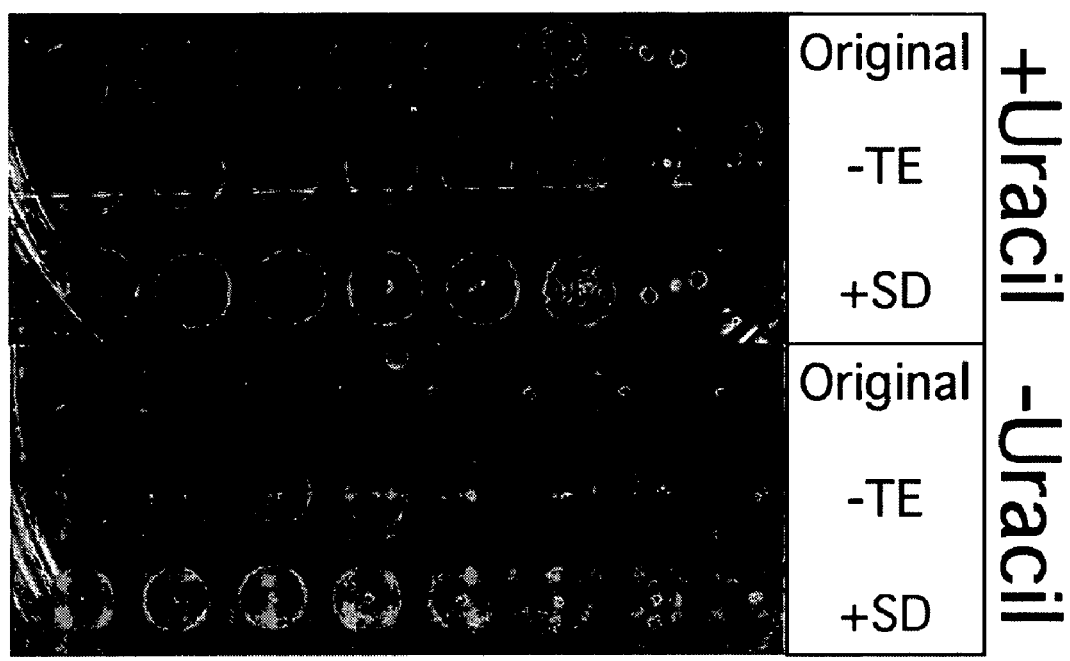
FIG. 4 is a representation of US0(ΔpyrF) (construct −TE) and US0(ΔpyrF) (construct SD+) cells maintained under various growth conditions.

Introduction of these two new constructs into the F' episome of US0(ΔpyrF) yielded higher basal levels of URA3 expression (FIG. 4, 10-fold serial dilutions of cells from left to right). Cells containing the original URA3 gene grew poorly in minimal media in the absence of uracil, but cells containing the –TE and +SD constructs displayed much stronger growth in the absence of uracil. These cells displayed higher sensitivity to 5-FOA, and consequently may prove to be useful for counter-selections in which the interactions being assayed (be they one hybrid, two hybrid, or three hybrid) are weak. This demonstrates the usefulness of altering codons to optimize the efficacy of a counterselectable system.

Example 4

Competitive Inhibition of the Prokaryotic Counterselectable System by 6-azauracil 6-azauracil (6AU) is metabolized into a competitive inhibitor (6-azauridine 5' phosphate) of the URA3 gene (Losson et al. (1981) Mol. Gen. Genet., 184:394-399; Levine et al.

(1980) Biochemistry, 19:4993-4999). 6AU has been used to modulate the activity of the URA3 gene in yeast (LeDouarin et al. (1995) Nucl. Acids Res., 23:876-878). Because 6AU is a competitive inhibitor of URA3, its ability to inhibit the URA3 step in uracil biosynthesis is a function of both the concentration of 6AU in the media and of the expression level of URA3. Consequently, it should be possible to tune the sensitivity of a yeast strain expressing a given level of URA3 to a fixed amount of 5-FOA by increasing the concentration of 6AU in the medium. In practice, this has not proven particularly effective in yeast (Vidal et al. (1996) Proc. Natl. Acad. Sci. USA, 93:10315-10320) because 6AU also blocks the synthesis of GTP (Exinger et al. (1992) Curr. Genet., 22:9-11). The reduction in UTP and GTP pools can lead to transcriptional arrest of RNA polymerase II (Lee et al. (2001) Mol. Cell Biol., 21:8651-8656; Nakanishi et al. (1995) J. Biol. Chem., 270:8991-8995; Shimoaraiso et al. (2000) J. Biol. Chem., 275:29623-29627).

Because bacteria are prokaryotes, their transcriptional machinery may be more tolerant to the effects of 6AU. Consequently, 6AU may prove to be a more effective reagent for modulating the activity of the URA3 gene in bacteria than in eukaryotic systems.

Figure 5:
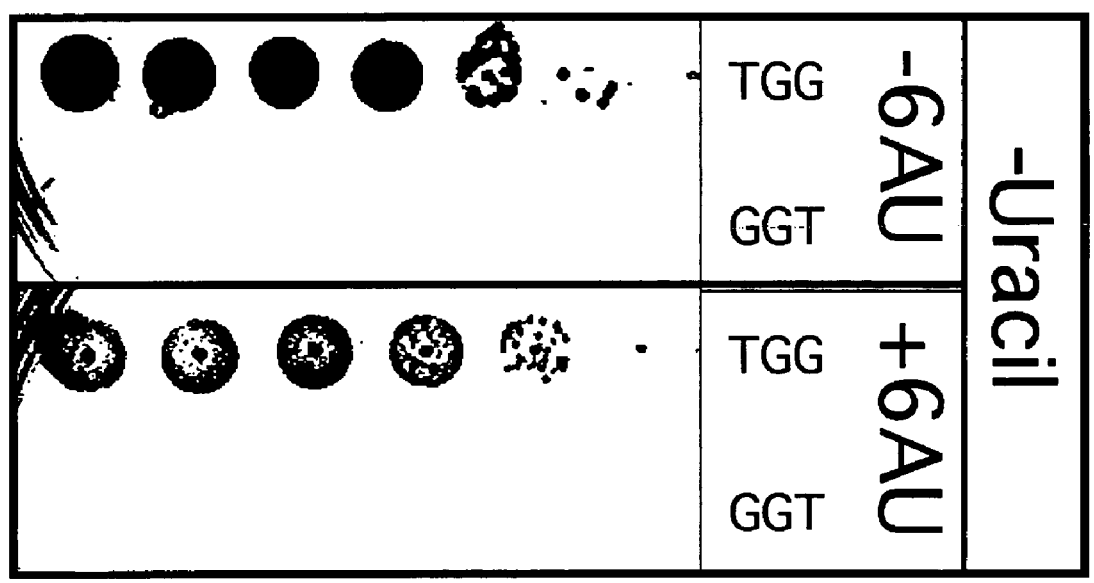
FIG. 5 is a representation of US0(ΔpyrF) cells maintained under various growth conditions.

To examine the ability of 6AU to inhibit the URA3 gene, the ability of a US0($\Delta$pyrF) strain containing the URA3 gene construct described above was tested in the F' episome with the "TGG" or "GGT" target sites, as described in Example 1, and the Zif268-cFos transcription factor (FIG. 5). In the absence of uracil, the "TGG" and "GGT" strains grew on minimal medium at different rates. The "GGT" strain displayed a significantly reduced rate of growth (FIG. 5, 10-fold serial dilutions of cells from left to right). When 6AU was introduced into the medium at a concentration of 0.5 µg/ml, the growth of the "GGT" strain was inhibited, but the growth of the "TGG" strain remained robust. These data demonstrate that 6AU can inhibit URA3 activity, which is expected to increase tolerance to 5-FOA. Thus, the URA3 gene/6AU combination can be used for positive selection. 6AU may also provide a method for tuning the sensitivity of bacteria to 5-FOA in the counterselectable system.

Example 5

Construction of a pHis3Ura3 Bicistronic Reporter Vector

In principle, it should be possible to create a library of random target sites in a plasmid that would represent prey DNA sequences in a one hybrid or two hybrid selection system to screen for interactions with a desired bait polypeptide. This principle has been exploited in a counterselectable one hybrid yeast system where a genomic promoter element is cloned into a promoter (bait) in yeast and a library of cDNAs (prey) are screened (Li and Hershkowitz (1993) Science, 262:1870-1874; Gstaiger et al. (1995) Nature, 373:360-362). However, the yeast selection system has not been used for the de novo selection of binding sites for a protein. One limitation of the yeast system is its transformation efficiency, which limits library sizes to $\sim 10^6$ clones. Transformation efficiencies in bacteria are much higher (approaching $10^{10}$ clones), which allows much more exhaustive searches of randomized sequences (e.g. $\sim 10^9$ clones are needed to construct a complete 15 bp randomized library).

When a prey library of randomized sequences in the promoter of a reporter gene was inserted upstream of the in the promoter of a reporter gene, a large number of constitutively activated promoters (0.01%) result. This rate of false positives can be prohibitive and is inefficient for screening. For example, when searching a library of $10^7$ sequences, this will result in around $10^3$ false positives. If the desired sequence in the prey library is rare relative to this number, it can be impossible to distinguish it from the background of false positives. To overcome this, both a selectable and counterselectable reporter gene were incorporated into a reporter vector in the bacterial selection system to select the true positives, and also to eliminate or greatly reduce the false positives.

Figure 6:
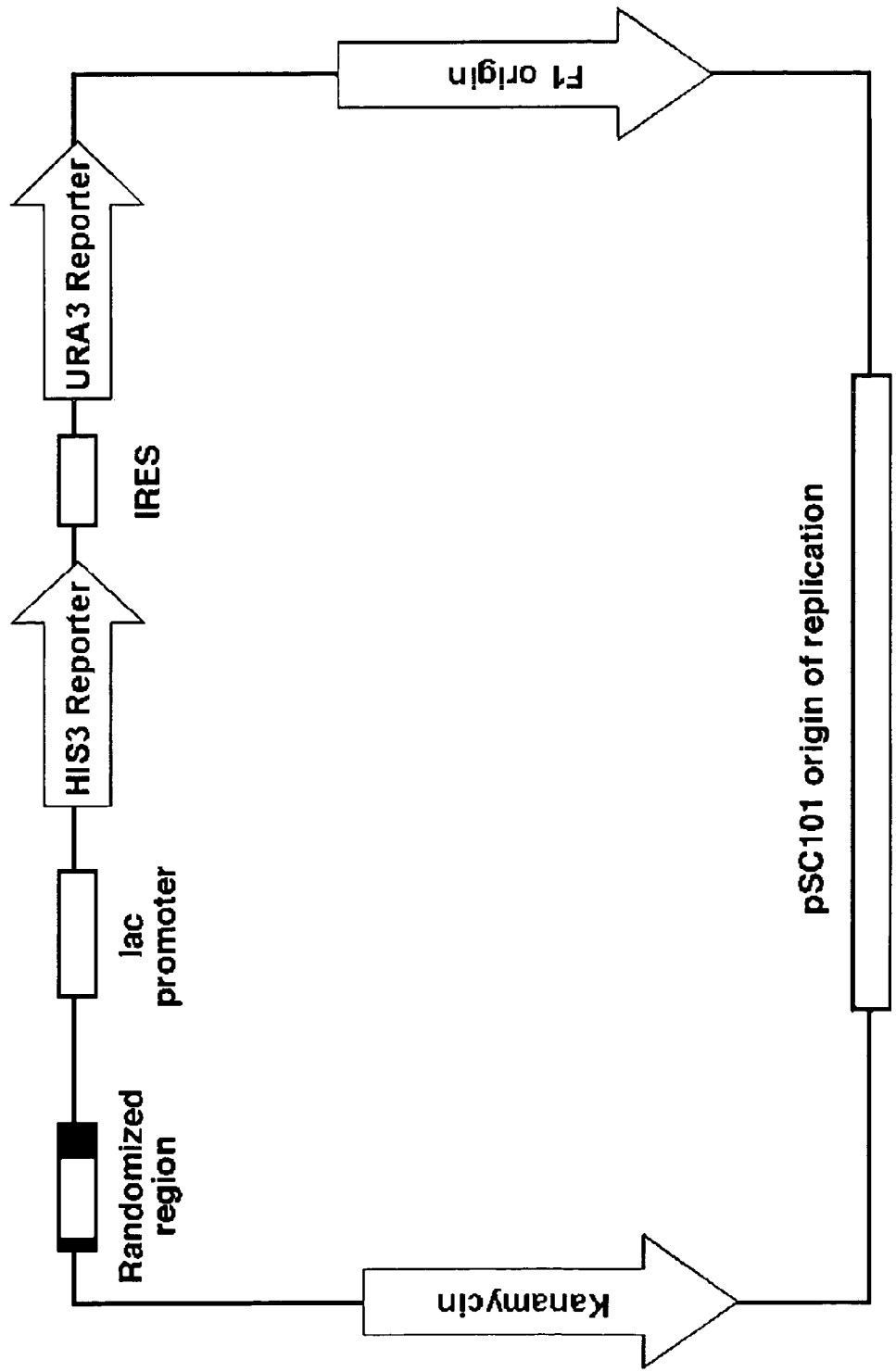
FIG. 6 is a schematic drawing of the pHis3Ura3 construct.

To accomplish this, a bicistronic reporter vector was created, pHis3Ura3, that is driven by a single lac promoter (FIG. 6). This reporter vector contains a selectable reporter gene, HIS3, and a counterselectable reporter gene, URA3. The lac promoter provides low levels of expression of both HIS3 and URA3. Translation of URA3 from the transcript is facilitated by the presence of its own Shine-Dalgarno sequence. Upstream of the lac promoter is a multiple cloning site for introduction of the randomized oligonucleotides for the construction of a prey reporter vector library. This reporter vector also contains a kanamycin resistance gene, a phage f1 origin, and a pSC101 origin of replication.

Maintaining a low copy number of the reporter vector inside bacteria is critical to maximizing the competition provided by the bulk genomic DNA of the bacteria that acts as a non-specific/pseudo-specific competitor. The pSC101 origin limits the copy number of the reporter vector to approximately 10 copies per cell (Lutz and Bujard (1997) Nucl. Acids Res., 25:1203-1210). Because of the competition provided by the bacterial genome, and because each bait is assayed independently, a single round of selection can be sufficient to isolate positive clones. Other low copy number origins of replication can be used and are known in the art. However, higher copy number reporters could potentially be useful for assaying DNA-binding proteins with low affinity. Thus, the new methods described herein relate to the use of constructs containing both selectable and counterselectable genes regulated by a single promoter.

Example 6

Method of Identifying a DNA Sequence that Interacts with a Protein

Figure 7:
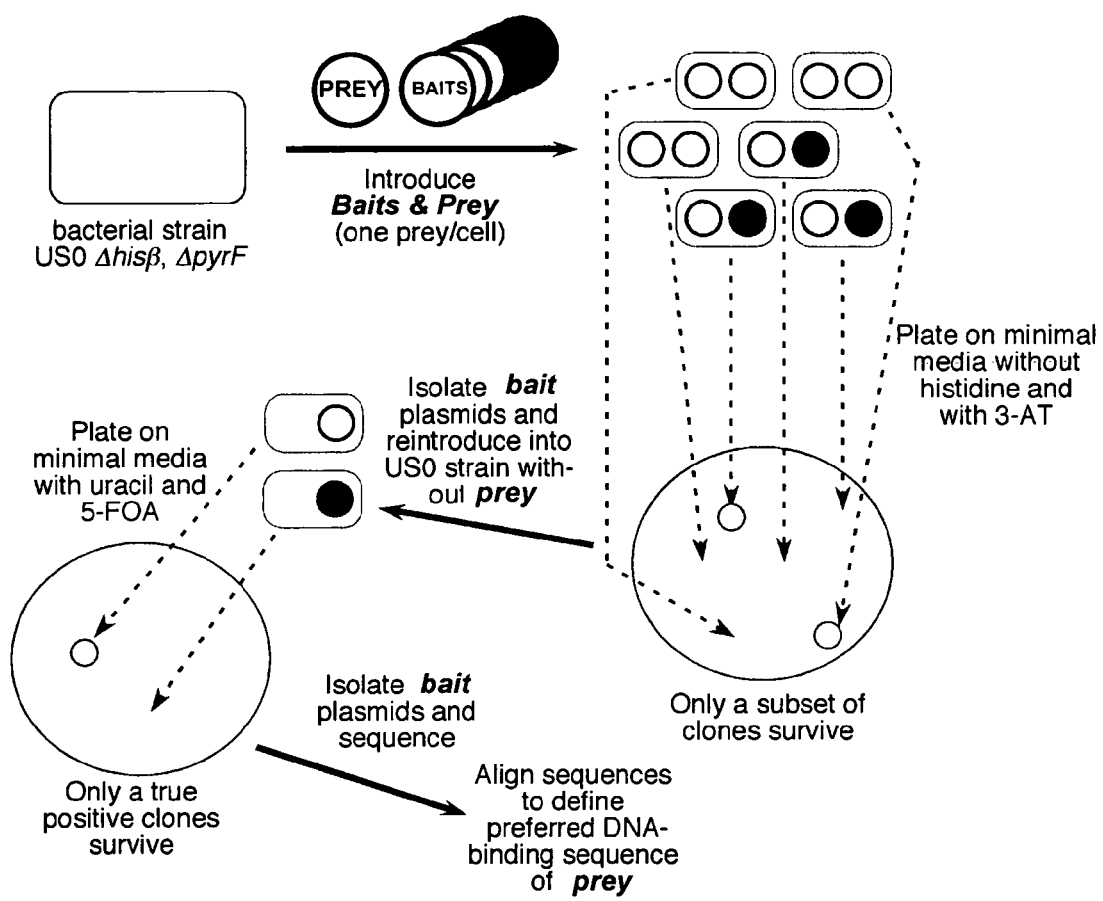
FIG. 7 is a schematic drawing of an in vivo double selection system.

In principle, a prey reporter vector library containing the pHis3Ura3 construct and a vector encoding a bait polypeptide are introduced into a bacterial selection strain that is auxotropic for hisB (a bacterial HIS3 homologue) and pyrF (a bacterial URA3 homologue). In the presence of the bait polypeptide, true positive clones produce a high level of HIS3, and thus tolerate growth on minimal medium in the absence of histidine and in the presence of 3-AT (FIG. 7). This stage of the selection eliminates the majority of the prey sequences, but false positive clones that express HIS3 at a high level due to an inherent property of the prey sequence, i.e., not dependent on the binding of the bait polypeptide, also survive under these selection conditions. The number of false positives recovered from the selection can significantly outnumber the number of true positives, especially if the true positives are relatively rare in the initial library.

The false positive clones are eliminated from this population by isolating the prey reporter vectors from the bacterial clones that survive the first round of selection. The prey reporter vectors can include a bacteriophage origin that is used to isolate the prey reporter vectors from M13 phage particles in the presence of helper phage. Alternatively, the bait polypeptide vector is selectively digested using a restriction enzyme that does not cleave the prey reporter vectors.

The bait reporter vectors are then reintroduced into the selection strain in the absence of the bait polypeptide. Cells containing the reporter vectors are then challenged by requiring growth in the presence of uracil and 5-FOA. False positive clones, in which the prey sequences are inherently active, are killed by the 5-FOA challenge. True positive clones, in which the reporter vector is inactive in the absence of the bait polypeptide, survive because they are insensitive to 5-FOA due to the low level of URA3 expression.

The prey reporter vectors selected in this manner are then isolated and sequenced using methods known in the art to determine the sequence of the randomized region. Alignment of multiple clones using an algorithm such as MEME or GRAM (Bailey and Elkan (1994) Proc. Int. Conf. Intell. Syst. Mol. Biol., 2:28-36; Bar-Joseph et al. (2003) Nat. Biotechnol., 21:1337-1342) is used to identify over-represented sequence motifs, which represent the DNA sequence binding site for the bait polypeptide. Thus, the two-step method of positive selection followed by negative selection can be used to identify a DNA sequence that interacts with a protein.

Example 7

Determination of the Consensus DNA Binding Sequence for Zif268 Using in Vivo Double Selection Library Construction Initially, an 18 base pair randomized library was built using pHis3Ura3 with each position fully randomized with all four bases. This bait reporter vector library was constructed by known methods employing restriction digestion/ligation and transformed into XL1-Blue electrocompetent cells. Following the recovery period from transformation, the number of transformed cells was determined by serial dilution to be approximately $2 \times 10^7$ unique clones. These plasmids (bait reporter vectors) were isolated as a pool by Maxiprep (Qiagen) to be transformed into the bacterial selection strain in conjunction with a bait transcription factor of interest.

Determination of Consensus Binding Sequences

For initial experiments, the $Cys_2His_2$ zinc fingers of Zif268 were used as the bait polypeptide. The DNA binding specificity of this protein has been determined previously by in vitro SELEX (Wolfe et al. (1999) J. Mol. Biol., 285:1917-1934). The $Cys_2His_2$ DNA-binding domain was fused directly to the alpha subunit of RNA polymerase in an expression plasmid with a chloramphenicol marker and a unique Xmn I restriction enzyme cleavage site (construct derived from pACL-alphaGAL4 and pBR-GP-Z123).

The Zif268 expression plasmid (bait expression plasmid) and the prey reporter vector library were introduced into the bacterial selection strain US0(ΔhisBΔpyrF) and put through the two steps of selection as in Example 6. In the selection step, $3.5 \times 10^7$ cells were plated on minimal plates containing 5 mM 3-AT, 200 μM uracil, and 10 μM IPTG. The bait expression plasmid was under control of the lac repressor, which allowed the expression level of the bait to be controlled by the concentration of IPTG in the media. Approximately 800 colonies survived the initial selection step. These colonies were harvested from the plate and, after a short recovery in rich media, they were midiprepped (Qiagen) to recover the plasmid DNA. The recovered plasmid DNA was a mixture of the bait expression plasmid and the surviving prey reporter vectors. These plasmids were treated with the restriction enzyme Xmn I to specifically digest the bait expression plasmid. This enzyme does not digest the prey reporter vector. Thus, the prey reporter vectors and bait expression plasmid constructs can readily be separated, e.g., by digesting the bait expression plasmid and/or by using agarose gel electrophoresis.

Figures 8A, 8B:
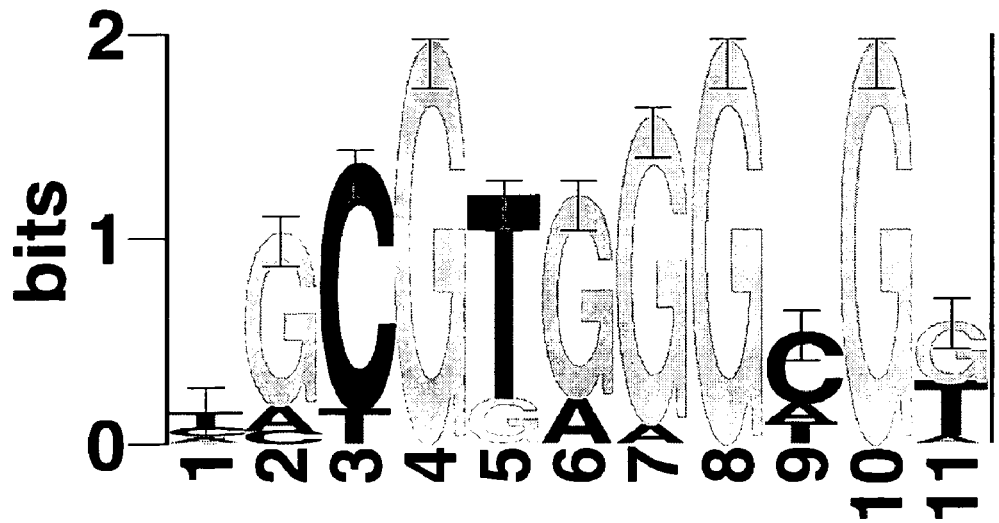
FIG. 8A is a list of raw unique sequences, SEQ ID Nos: 18-33 respectively, from Zif268 in vivo double selection experiments.
FIG. 8B is a sequence logo display of information content at each position in the binding site for the 16 sequences aligned by MEME (Bailey and Elkan (1994) Proc. Int. Conf. Intell. Syst. Mol. Biol., 2:28-36). A "sequence logo" is a schematic way of displaying the patterns in a set of aligned sequences and the frequency of bases at every position (Schneider and Stephens (1990) Nucl. Acids Res., 18:6097-6100).

After purifying the uncut prey reporter vectors, they were reintroduced into the selection strain. Approximately 60,000 cells were plated on M9 minimal plates containing 0.1% yeast extract, zinc sulfate, calcium chloride, thiamine, magnesium sulfate, 0.2 mM uracil, and 2 mM 5-FOA. Two hundred sixty colonies survived this counterselection step. Seventeen of these clones were miniprepped and sequenced. Sixteen of the clones contained unique sequences (FIG. 8A). These sequences were analyzed using the MEME algorithm which identified a sequence motif that was the previously defined recognition sequence for Zif268 (Wolfe et al. (1999) J. Mol. Biol., 285:1917-1934). These data are presented in a sequence logo format (Schneider and Stephens (1990) Nucl. Acids Res., 18:6097-6100) (FIG. 8B; the maximum possible content at each position is 2 bits and the expected sequence for Zif268 is gGCGTGGGCGt; SEQ ID NO:4).

A "sequence logo" is a schematic way of displaying the patterns in a set of aligned sequences. The characters representing the sequence are stacked on top of each other for each position in the aligned sequences. The height of each letter is made proportional to its frequency, and the letters are sorted so the most common one is on top. The height of the entire stack is then adjusted to signify the information content of the sequences at that position. From these sequence logos, one can determine not only the consensus sequence but also the relative frequency of bases and the information content (measured in bits) at every position in a site or sequence. The logo displays both significant residues and subtle sequence patterns (see, e.g., Schneider and Stephens (1990) Nucl. Acids Res., 18:6097-6100).

These data demonstrate the efficacy of the double-selection method for efficient identification of binding sequences and that such information can be used to identify, e.g., a conserved binding sequence. The constructs for use in the method can, as demonstrated herein, be designed so that the bait and prey constructs can be distinguished and separated based on incorporation of a unique restriction site into one of the two constructs (i.e., the restriction site is contained in one construct and not in the other).

Example 8

Determination of the Consensus DNA Binding Sequence for Zif268-cFos Using in Vivo Double Selection To test the flexibility of the in vivo double selection system, the ability of the system to be used to determine the preferred binding sequence of a homodimeric zinc finger protein, Zif268-cFos, was examined. This protein contains fingers 2 and 3 of Zif268 fused to a leucine zipper that facilitates the binding of the protein to a palindromic sequence composed of GCGTGG(g/t) that has a two base pair overlap at the center of the sequence (Wolfe et al. (2000) Structure, 8:739-750). The gene encoding this protein was cloned into pBR-GP-Z123 to express Zif268-cFos as a fusion to Gal11P. This protein, when co-expressed with α-GAL4 (GAL4 fused to the α subunit of RNA polymerase), can activate a LacZ reporter in the bacterial two-hybrid system. Together, the Gal11P-Zif268-cFos and α-GAL4 constructs function as the prey, and a prey expression plasmid was generated, as in Example 7.

The prey reporter vector library described in Example 7 and the bait expression plasmid were introduced into the US0(ΔhisBΔpyrF) selection strain and put through the two selection stages described in Example 6. In the selection step, $5\times10^7$ cells were plated on minimal plates containing 5 mM 3-AT, 200 μM uracil, and 10 μM IPTG Approximately 600 colonies survived the initial selection step. These colonies were harvested from the plate and, after a short recovery in rich media, they were miniprepped (Qiagen) to recover the plasmid DNA. These plasmids were treated with the restriction enzyme Xmn I to specifically digest the bait expression plasmid. After purifying the uncut bait reporter vectors, they were reintroduced into the selection strain. Approximately 400,000 cells were plated on minimal plates containing 0.1% YM and 2 mM 5-FOA. 900 colonies survived the counterselection step.

Fifty four clones from this stage were miniprepped and sequenced. Twenty-four of these clones contained unique sequences (FIG. 9A). The unique sequences were analyzed using the MEME algorithm, which identified a sequence motif in 17 of the clones that represented the expected recognition sequence for Zif268-cFos (Wolfe et al. (2000) Structure, 8:739-750) (FIG. 9B; the maximum possible content at each position is 2 bits and the expected sequence for Zif268-cFos is (a/c)CCACGCGTGG(t/g); SEQ ID NO:5). However, there was more noise in the sequences (7 of 24 sequences did not contain an obvious motif) compared to those obtained in determining the DNA consensus binding site for Zif268 described in Example 7. With the use of an algorithm such as MEME, this level of noise does not create a problem because the MEME analysis discards a subset of sequences that does not contain a given motif, thus permitting the effective use of this system with this level of noise.

Example 9

Figure 10:
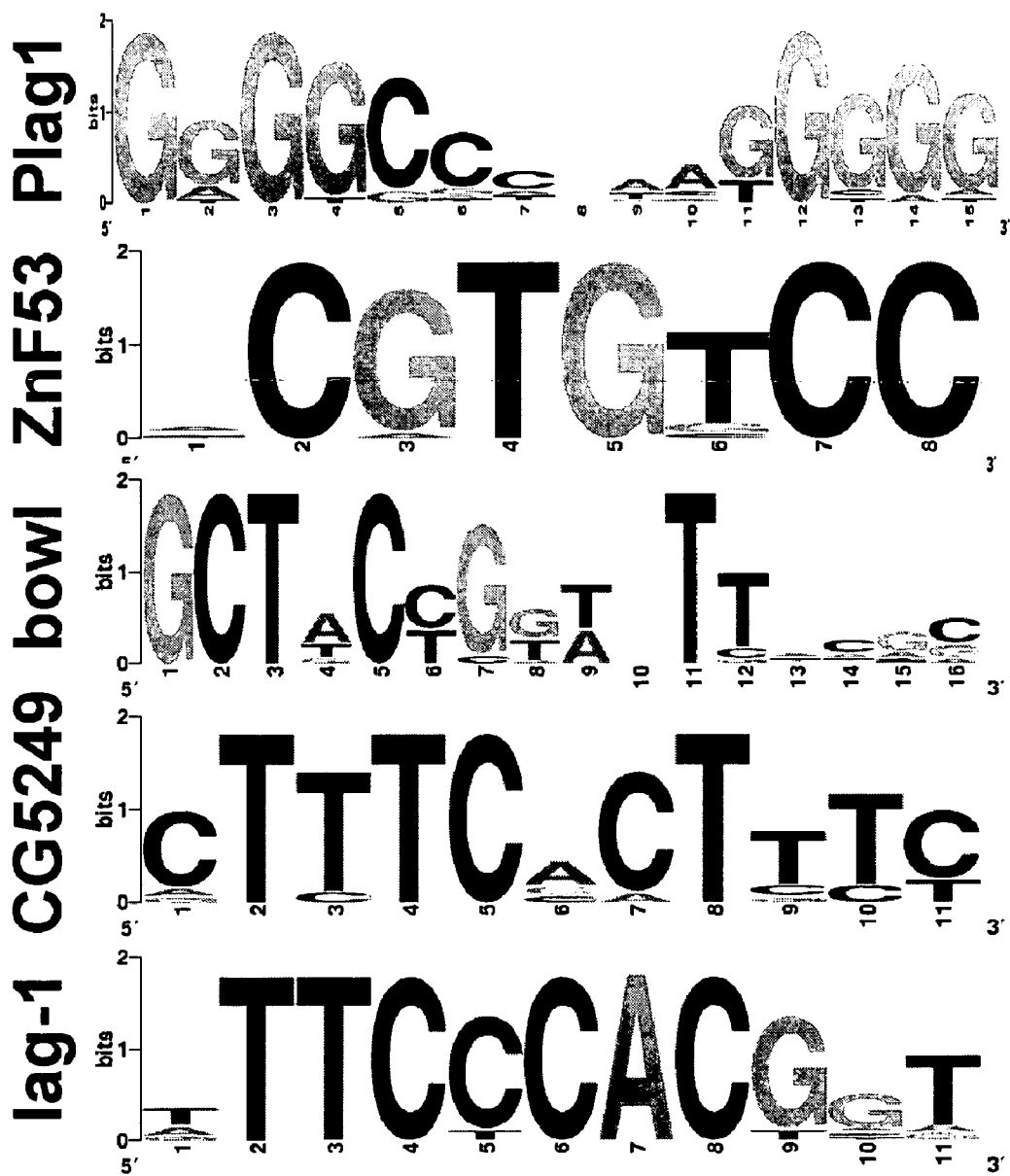
FIG. 10 is a series of four sequence logos as described herein that represent binding site signatures for four zinc finger proteins (Znf53, Bowl, CG5249, and Plag1) and one Rel homology region protein (LAG-1) assayed using the selection system.

Determination of the Plag1 DNA Binding Specificity Using a Two-Step Selection Procedure The DNA-binding specificity of Plag1 was determined using a two-step selection procedure using the bacterial one-hybrid system described herein. The previously described Plag1 consensus sequence is GGRGGCCNNNNNNRGGK (SEQ ID NO:1) (Hensen et al. (2002) Cancer Res., 62:1510-1517). Plag1 is a proto-oncogene that contains seven zinc fingers (Hensen et al. (2002) Cancer Res., 62:1510-1517). DNA recognition appears to be primarily mediated by two subsets of the fingers (fingers 2 through 4 and fingers 6 and 7) with some variability permitted in the spacing between the recognition elements bound by these subsets of fingers (Hensen et al. (2002) Cancer Res., 62:1510-1517; Voz et al. (2000) Cancer Res., 60:106-113). $Cys_2His_2$ zinc fingers 1 through 7 from Plag1 were fused via a 23 amino acid flexible linker directly to the alpha subunit of RNA polymerase in the vector pACL-αgal4 (Joung et al. (2000) Proc. Natl Acad. Sci. USA, 97:7382-7387) to generate the bait. This bait was introduced into the selection strain and these cells were made electrocompetent. Electrocompetent cells containing bait vector were transformed with the original prey plasmid library and grown in SOC medium for one hour at 37° C. Then the cells were pelleted, resuspended in NM medium and grown at 37° C. for one hour. Finally, the cells were washed four times with sterile water, once with NM solution with 200 μM Uracil, resuspended in NM medium with 200 μM Uracil, and plated on NM positive selection plates. Approximately $7.6\times10^7$ cells were selected on two His-selective plates with 3 mM 3-AT for ~48 hours at 37° C. until well-defined colonies were visible on the plates. Approximately 5,000 colonies survived in the positive selection. These cells were harvested as a pool and the plasmid DNA from these cells was isolated. The resulting mixture of bait and prey plasmids were digested with XmnI, which specifically cleaves the bait plasmid, and then transformed into the selection strain for the 5-FOA counter-selection. For the negative selection, $2\times10^6$ cells were selected on 2 mM 5-FOA selective plate at 37° C. for one day and about 5,000 colonies survived. Forty-eight clones were sequenced and 23 were unique (the remains were replicates). Individual colonies were picked from the plate for prey isolation and sequencing of the randomized region. The sequences of 23 unique clones were analyzed using both the MEME algorithm and BIOPROSPECTOR® to identify over-represented sequence motifs. Gaps of 1, 2, and 3 bp were present between the two different recognition motifs found in this analysis, with the 2 bp gap being preferred, based on its frequency of occurrence. The identified over-represented motif was used to build the resulting sequence logo representing its DNA-binding specificity. The binding site signature determined using the bacterial selection system is consistent with the previously described DNA-binding specificity of Plag1 determined by in vitro SELEX (Hensen et al.; Voz et al.) (FIG. 10). Thus, the bacterial selection system can identify the recognition sequence of both simple target sites and more complicated recognition motifs, e.g., motifs recognized by multiple zinc fingers subsets.

Example 10

Use of a Rarified Library Reduces the Selection Procedure to a Single Step

The order of the positive and negative selection steps for a library of DNA binding sequences was inverted. By performing the negative selection first, the library was purged of the majority of the false positive clones before it was used in the presence of the transcription factor bait to isolate target sites (prey) that were recognized by the protein. Instead of performing two steps of selection (for example, positive selection with 3-AT followed by negative selection with 5-FOA) for identifying a DNA binding sequence that binds to a given bait, the negative selection was performed once to generate a "rarified library" and this library was then used for subsequent selections with different baits. This allowed the DNA-binding specificity of various baits to be determined in a single selection step.

To test the feasibility of this approach, a rarified prey library was generated by transforming the selection strain with an original prey library (described in Example 7) and plating these cells on selective media containing 5-FOA. Specifically, transformants ($7.8\times10^7$) of the selection strain containing the original prey library were screened on square plates (245 mm×245 mm) containing 2 mM 5-FOA. The plates were incubated at 37° C. for one day and surviving cells were harvested and the prey plasmids were recovered to generate the rarified prey library containing ~$10^7$ clones.

Next, to determine if the negative selection reduced the number of false positive prey, the selection strain was electroporated with either the original prey library or the rarified prey library and ~$10^7$ transformants from each population were plated under positive selection conditions (2 mM 3-AT) in the absence of a bait and grown at 37° C. Approximately 7000 colonies survived from the original library whereas only about 80 colonies survived from the rarified library. Thus, the counterselection procedure reduced the false positive rate in the rarified library by about two orders of magnitude.

The URA3 reporter is also very effective in the bacterial one-hybrid system. The false positive rate of the original library and the "rarified" library were compared. The number of false positive clones in the rarified library was reduced by a factor of ~$10^3$.

A pilot screen was performed with the Zif268 bait using a single positive selection procedure and the rarified prey library. $Cys_2His_2$ zinc fingers 1 through 3 from Zif268 were fused via a 23 amino acid flexible linker directly to the alpha subunit of RNA polymerase in the vector pACL-αgal4 (Joung et al. (2000) Proc. Natl. Acad. Sci. USA, 97:7382-7387) to generate the bait. This bait was introduced into the selection strain and these cells were made electrocompetent. Electrocompetent cells containing bait vector were transformed with the rarified prey plasmid library and grown in SOC medium for one hour at 37° C. The cells were then pelleted, resuspended in NM medium, and grown at 37° C. for one hour. Finally, the cells were washed four times with sterile water, once with NM solution with 200 µM Uracil, resuspended in NM medium with 200 µM Uracil, and plated on NM positive selection plates. Approximately $1\times10^7$ cells containing the bait and prey library were screened on 5 mM 3-AT containing NM plates. Cells were grown for ~48 hours at 37° C. until well-defined colonies were visible on the plates. Ten individual colonies were picked, subcultured, and the plasmid DNA isolated by miniprep. The randomized region of each prey was then sequenced. Nine of the ten clones contained Zif268 target sites. The sequences of all unique clones were analyzed using the MEME algorithm (Bailey and Elkan (1994) Proc. Int. Conf. Intell. Syst. Mol. Biol., 2:28-36) to identify over-represented sequence motifs. The Zif268 binding sites were present in 7 of 8 unique clones (expectation value: 3.0e-06; sites bolded, see Table 1).

TABLE 1

DNA Binding Sites Isolated from Zif268 Selection Using a Rarified Library

| | |
|---|---|
| CCACACCCACGCAGTACA | (SEQ ID NO:7) |
| ATGCTTGTCGCTACGTGG | (SEQ ID NO:8) |
| AACCTCCCACGCAGGCTG | (SEQ ID NO:9) |
| CCGCCTACGCAATGTCCA | (SEQ ID NO:10) |
| TTCCGCCCACACACGCGG | (SEQ ID NO:11) |
| CACGCCCACGTGGGGCAA | (SEQ ID NO:12) |
| GACGCCCACACGTGCGAG | (SEQ ID NO:13) |
| CACGCCCACGTGGATAGT | (SEQ ID NO:14) |

Thus, the order of the positive and negative selection steps can be inverted to generate a rarified library useful for identifying DNA binding signatures for a zinc finger protein, Zif268.

Example 11

Use of the Rarefied Library to Determine the DNA Binding Specificity of Znf53

The rarefied library described in Example 10 was used to determine the DNA binding specificity of four $Cys_2His_2$ zinc finger proteins (Znf53; Bowl; CG5249; and Odd-skipped) to confirm its utility for use in a single selection step.

The single-step selection procedure was performed using a zinc finger protein, ZnF53, as the bait. ZnF53 contains three zinc fingers that were previously selected by phage display to recognize a portion of the p53 recognition sequence (Wolfe et al. (1999) J. Mol. Biol., 285:1917-1934; Greisman and Pabo (1997) Science, 275:657-661). $1.5\times10^7$ cells transformed with the rarified prey library in the presence of ZnF53 bait were screened on minimal media plates containing 2 mM 3-AT. DNA from twenty clones of the approximately 3,600 survivors was isolated and sequenced. All of these sequences were unique and contained a ZnF53 recognition element (Wolfe et al.) based on MEME analysis (FIG. 10). Based on previous in vitro analysis, the preferred Znf53 binding sequence is aCGTGTC(c/t) (Wolfe et al. (1999) J. Mol. Biol., 285:1917-1934). Thus, a rarified library can be used to identify DNA binding signatures for a different zinc finger protein, Znf53.

Example 12

Use of the Rarefied Library to Determine the DNA Binding Specificity of Bowl

The rarefied library described in Example 10 was used to determine the DNA binding specificity of Bowl, a *D. melanogaster* zinc finger protein (FIG. 10). The gap between the Bowl recognition elements is typically 0 or 1 base pair, although 2, 3, and 4 bp gaps were also observed based on a BIOPROSPECTOR® (Liu et al. (2001) Pac. Symp. Biocomput., 127-138) analysis.

$Cys_2His_2$ zinc fingers 1 through 5 for bowl were fused via a 23 amino acid flexible linker directly to the alpha subunit of RNA polymerase in the vector pACL-αgal4 (Joung et al. (2000) Proc. Natl. Acad. Sci. USA, 97:7382-7387) to generate the bait. This bait was introduced into the selection strain and these cells were made electrocompetent. Electrocompetent cells containing bait vector were transformed with the rarified prey plasmid library and grown in SOC medium for one hour at 37° C. The cells were then pelleted, resuspended in NM medium, and grown at 37° C. for one hour. Finally, the cells were washed four times with sterile water, once with NM solution with 200 µM Uracil, resuspended in NM medium with 200 µM Uracil, and plated on NM positive selection plates. Approximately $1\times10^7$ cells containing the bait and prey library were screened on 5 mM 3-AT containing NM plates. Cells were grown for ~72 hours at 37° C. until well-defined colonies were visible on the plates. Forty-eight colonies survived. Individual colonies were picked, subcultured, and the plasmid DNA isolated by miniprep. The randomized region of each prey was then sequenced. The sequences of all unique clones were analyzed using the MEME algorithm and BIOPROSPECTOR® to identify over-represented sequence motifs. For Bowl, 16 unique sequences contained an over-represented motif and were used to build the resulting sequence logo representing its DNA-binding specificity.

Bowl contains five $Cys_2His_2$ zinc fingers, four of which are highly homologous to the fingers in Odd. As a consequence, the core DNA-binding specificity of Bowl is similar to that of Odd. However, the Bowl binding site signature contains an additional recognition element, likely due to its additional zinc finger, that may define a subset of Odd binding sites that are recognized by Bowl. This additional recognition sequence is absent from the selected Odd binding sites. Thus, the rarified library and methods described herein can be used to differentiate the DNA binding signatures of proteins with highly similar DNA binding specificities.

Example 13

Use of the Rarefied Library to Determine the DNA Binding Specificity of CG5249

The rarefied library described in Example 10 was used to determine the DNA binding specificity of CG5249, a *D. melanogaster* zinc finger protein (FIG. 10). CG5249 contains five zinc fingers, four of which are homologous to the fingers in its vertebrate homolog, Prdm1/Blimp1. Cys2His2 zinc fingers 1 through 5 for CG5249 were fused via a 23 amino acid flexible linker directly to the alpha subunit of RNA polymerase in the vector pACL-αgal4 (Joung et al PNAS 2000, 97: 7382-7387) to generate the bait. This bait was introduced into the selection strain and these cells were made electrocompetent. Electrocompetent cells containing bait vector were transformed with the rarefied prey plasmid library and grown in SOC medium for one hour at 37° C. The cells were then pelleted, resuspended in NM medium, and grown at 37° C. for one hour. Finally, the cells were washed four times with sterile water, once with NM solution with 200 µM Uracil, resuspended in NM medium with 200 µM Uracil, and plated on NM positive selection plates. Approximately $2 \times 10^7$ cells containing the bait and prey library were screened on 5 mM 3-AT containing NM plates. Cells were grown for ~48 hours at 37° C. until well-defined colonies were visible on the plates. Approximately 80 colonies survived. Individual colonies were picked, subcultured, and the plasmid DNA isolated by miniprep. The randomized region of each prey was then sequenced. The sequences of all unique clones were analyzed using the MEME algorithm to identify over-represented sequence motifs. For CG5249, 14 unique sequences contained an over-represented motif and were used to build the resulting sequence logo representing its DNA-binding specificity. The binding site signature determined for CG5249 is similar, but not identical, to the DNA-binding specificity previously determined for Prdm1/Blimp1 based on identified in vivo recognition sequences and SELEX data (Kuo and Calame (2004) J. Immunol., 173:5556-5563). Key features of the CG5249 binding site signature have been confirmed by analysis of point mutations in this site in the bacterial one-hybrid system.

Figures 11A, 11B:
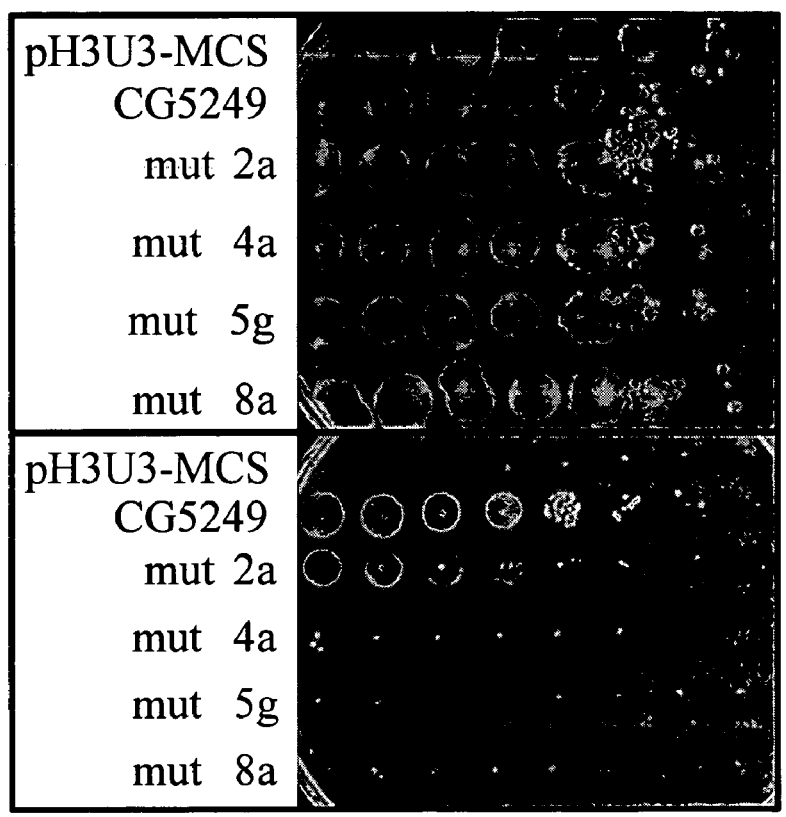
FIGS. 11A and 11B are representations of growth plates that show the mutational analysis of the CG5249 consensus sequence. 11A shows cells grown on rich media and 11B shows the cells grown on minimal media containing 3-AT (3-amino 1,2,4-triazol).

To test the binding specificity of CG5249, single point mutations were introduced at positions 2, 4, 5, and 8 of the consensus sequence in appropriate prey vectors (mut 2a; 4a; 5g; 8a; where 2a indicates that position 2 of the CG5249 consensus has been mutated to an A). The activity of these mutant prey in the presence of the CG5249 bait were compared to a prey containing the consensus sequence with the CG5249 bait (CG5249). The activity of a prey without a CG5249 binding site (pH3U3-MCS) with the bait was also assayed as a control. Briefly, each combination of bait and prey were electroporated into the selection strain and grown in SOC medium for one hour at 37° C. Then the cells were pelleted, resuspended in NM medium, and grown at 37° C. for one hour. Finally, the cells were washed four times with sterile water, once with NM solution with 200 µM Uracil, and resuspended in NM medium with 200 µM Uracil. These cells were titred in ten-fold dilutions on rich media (FIG 11A) or on 3-AT containing minimal media (FIG. 11B). Only the CG5249 prey grew robustly on selective media. Mutations at each of the four positions in the consensus sequence severely reduced the ability of the CG5249 bait to survive with the mutant preys under selective conditions. Mutation 2a reduced the growth rate of the cells and the other mutations abolished survival. Thus, the rarified library and methods described herein can be used to identify the relevance of specific residues in a DNA binding protein'DNA binding site signature.

Example 14

Use of the Rarefied Library to Determine the DNA Binding Specificity of LAG-1

The rarefied library described in Example 10 was used to determine the DNA binding specificity of a non-zinc finger protein (LAG-1) to confirm its utility for use in a single selection step for DNA binding proteins other than zinc finger proteins.

The *C. elegans* protein LAG-1 contains a Rel-homology region (RHR) DNA binding domain. The DNA binding specificity of the human homolog of LAG-1, RBP-Jκ, has been defined by SELEX (Tun et al. (1994) Nucl. Acids Res., 22:965-971) as (g/t)TTCCCACG(g/c)t (SEQ ID NO:6). The ability of LAG-1 to recognize the core recognition element in this sequence has been confirmed by gel shift assay (Christensen et al. (1996) Development, 122:1373-1383). Using the conserved Rel homology region from LAG-1 as the bait, $1.2 \times 10^7$ cells were screened with the rarefied plasmid library on 3 mM 3-AT. Approximately 80 colonies survived. From 17 sequenced unique clones, 12 contain the LAG-1 DNA-binding signature identified previously (FIG. 10). The LAG-1 signature can have 1, 2, or 3 base pairs between the two sequence motifs, only a one base pair gap is shown at position 8.

The binding site signature determined for the RHR from LAG-1 is similar to the previously determined specificity of RBP-Jκ. These results confirm that a rarified prey library can be used to accelerate the selection process for the identification of binding site signatures for both zinc finger and non-zinc finger DNA-binding domains.

Example 15

Correction for Codon Bias in Use of the Rarefied Library to Determine the DNA Binding Specificity of Odd-skipped The four zinc fingers from Odd were fused to the RNA polymerase α subunit to generate the bait for binding site selection. However, the initial selections with the Odd bait were unsuccessful with only a small number of clones (background) surviving the selection. Subsequent analysis by Western blot of the Odd bait revealed that the majority of the fusion protein was expressed as a truncated form. Poor expression of eukaryotic proteins in bacteria frequently results from differences in codon bias (Kane (1995) Curr. Opin. Biotechnol., 6:494-500); consequently, ten poorly utilized codons in Odd were changed to preferred synonymous codons. These changes resulted in a dramatic increase in the expression level of full-length bait protein. Thus, correction of codon bias can increase yields of proteins used in the selection/counterselection methods of the present invention.

Example 16

Stringency of Selection Conditions Can Affect Binding Motif Signatures Obtained from the Bacterial Selection Systems The recoded Odd bait was used for binding site selections in the bacterial one-hybrid system. These selections were performed at three different stringencies (1.5 mM, 2.5 mM, and 5 mM 3-AT) to examine the effect that different selective pressures have on the information content of the resulting binding site signature (i.e., the DNA binding site specificity information).

The influence of the selection conditions on the accuracy of the DNA-binding specificity ("binding site signature") that is realized using the bacterial one-hybrid system was determined. Setting the selection stringency at a high threshold provided a binding site signature that was composed of only the highest affinity sites, and thus, some of the information about the relative energetic impact of mutations in the preferred binding site could have been lost. The signature was expanded by performing the selections at lower stringencies. Each signature was compiled from >20 sequences that contained a binding site based on MEME analysis.

In general, the signature produced at each stringency was similar (FIG. 12): Roughly the same 9 base pair motif was identified in each case. However, the binding site signatures generated at 1.5, 2.5, and 5 mM 3-AT provided different impressions for the relative penalty for mutating each of the first five positions of the preferred recognition sequence. For example, at 5 mM 3-AT, the first five bases in the signature were absolutely conserved. However, at 2.5 mM and 1.5 mM 3-AT, both A and T appeared to be tolerated to varying degrees at position 4 (FIG. 12, boxed).

Figure 12:
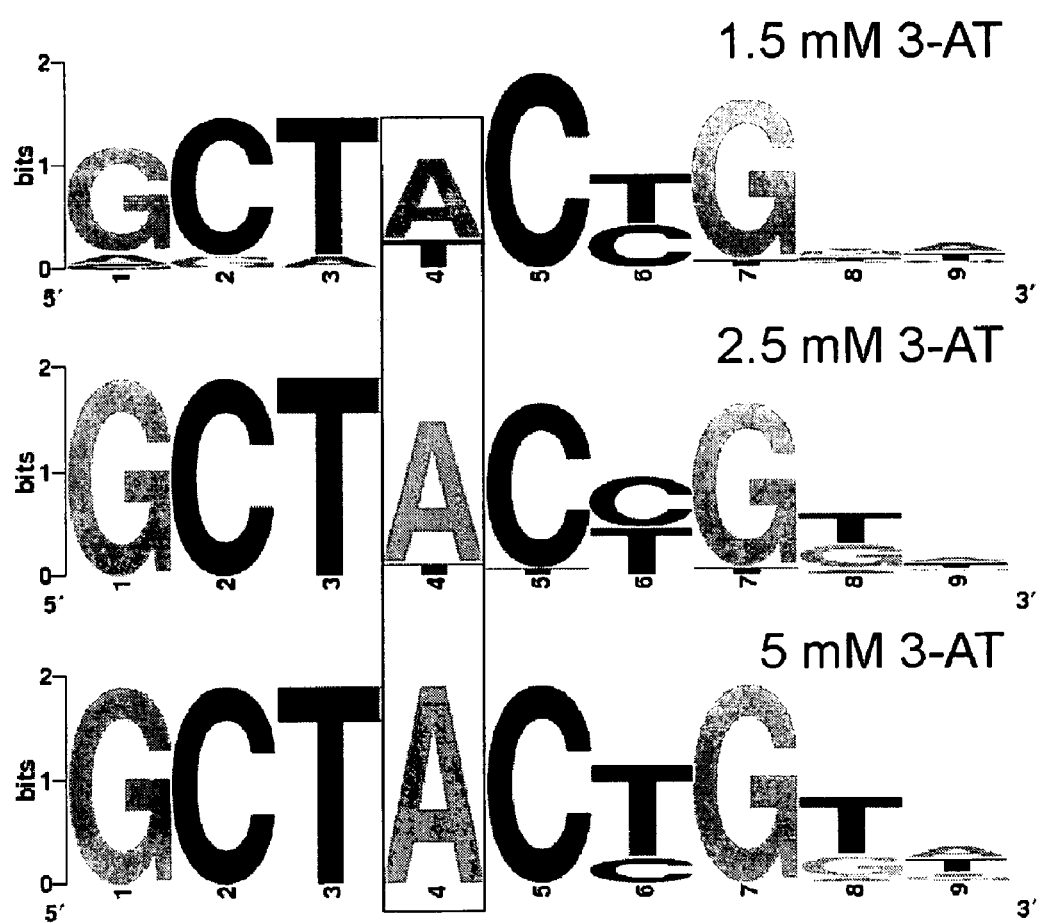

The bacterial one-hybrid system was used to investigate the importance of mutations at different positions within the Odd consensus sequence (FIG. 12). Point mutations were independently introduced at each of the first five positions of the Odd consensus sequence in a prey vector. The survival and growth rates of cells containing the Odd bait and each mutant prey were then evaluated in comparison to the consensus Odd prey at various 3-AT concentrations. The effect of individual mutations on the survival and growth rates at different 3-AT concentrations was striking. At 5 mM 3-AT, only the conservative A to T mutation at position 4 conferred survival at a rate that was comparable to the Odd consensus sequence, and cells containing this mutant prey displayed an attenuated growth rate. At 1 mM 3-AT, the growth rate for cells containing the position 4 mutation was comparable to the Odd consensus prey.

Moreover, at 1 mM 3-AT, mutations to positions 1 and 3 of the consensus sequence were partially tolerated; these mutant prey were unviable at 5 mM 3-AT. Odd prey containing mutations at position 2 and 5 were essentially unviable under both sets of conditions.

In vitro gel shift assays were used to validate the Odd binding site signature and to confirm the relative importance of mutations within the Odd consensus sequence. Purified Odd protein shifts an oligonucleotide containing the consensus sequence (FIG. 13). For each competition shift, 2.5 µM cold competitor was added to the binding reaction. "wt" denotes the consensus sequence GCTACTGTA embedded in a larger oligonucleotide. The other competitors have mutations at each of the first five positions of the consensus sequence where the number represents the position and the letter represents the substitution. For example, "1c" denotes cCTACTGTA. Excess cold competitor containing the Odd consensus sequence effectively competed away the shifted probe. Competition with an identical concentration of cold competitor containing each of the five mutations described above reduced the amount of shifted probe to an extent that was consistent with the one-hybrid mutagenesis experiments. For example, the cold competitor containing the A to T mutation at position 4 competed almost as effectively as the consensus cold competitor. In contrast, the C to G mutation at position 5 proved ineffective in competing away the shifted labeled consensus site. Thus, the survival rates of bacteria at lower selection stringencies more accurately reflect the tolerance of Odd to different mutations within its preferred recognition sequence.

Example 17

Use of the Bacterial Selection System to Determine the Function of Different Domains in a DNA Binding Protein The bacterial selection system can also be used to analyze the importance of different domains for the function of a DNA binding protein, such as a transcription factor. For example, only the first seven base pairs of the Odd binding site signature are highly conserved. However, Odd would be expected to recognize approximately a twelve base pair site if all four of its zinc fingers are recognizing the DNA in a manner similar to Zif268. Based on the known recognition properties of other zinc finger proteins, it is possible to crudely predict which zinc fingers are contributing to DNA recognition. An analysis of Odd suggests that fingers 1 and 2 are the primary determinants of specificity, while finger 3 may provide a modest contribution to the specificity at the 3' end of the target sequence. There is no evidence that finger 4 contributes to the signature based on its preferred recognition sequence.

To test these predictions, three deletion constructs were generated in which one or more fingers were removed from the Odd bait. The activity of each truncated bait was compared to the four-finger protein in the bacterial selection system (FIG. 14). A prey vector containing the consensus Odd binding site was combined with various baits containing different numbers of zinc fingers from Odd to assess which fingers are critical for DNA recognition. "Ck" represents the empty bait vector (no Odd fingers); F1-F4 contains all four odd fingers; the other three constructs represent different N- or C-terminal truncations of Odd. For example, F1-F3 is missing finger 4. The cells were plated on minimal media (top panel) or on selective media that contained 5-FOA.

As anticipated, removing finger 1 abolished the activity of the Odd bait, whereas removing finger 4 resulted in only a modest change in activity of the Odd bait. Removing fingers 3 and 4 resulted in only a modest additional decrease in activity when compared to the finger 4 deletion. As depicted in the bottom panel (FIG. 14), the presence of fingers 1 and 2 appeared to provide the majority of the DNA-binding specificity for this protein. The growth rate of the F1-F2 bait was only somewhat slower that the F1-F4 bait, whereas cells containing F2-F4 bait did not survive. Based on this analysis, fingers 1 and 2 of Odd are the primary determinants of DNA-binding specificity. These results also further demonstrate the high specificity of the bacterial one-hybrid system in determining protein-DNA interaction.

Example 18

Counter-Selectable Marker for the One/Two/Three Hybrid System in Bacteria

Several experiments have focused on examining the level of enrichment of desired clones above background that can be obtained in a single round of selection. Two additional factors were investigated with regards to the counterselection system. First, the growth medium used under selective conditions to optimize the sensitivity of the cells to 5-FOA was improved. Second, experiments were performed to determine the degree of enrichment that can be obtained in one and two rounds of selection.

Two different types of minimal medium conditions were investigated: His-selective medium (NM), which is the minimal medium that is reported with the original bacterial two-hybrid system (Joung et al. (2000) Proc. Natl. Acad. Sci. USA, 97:7382-7387), and M9 minimal medium supplemented with yeast extract (YM). For 5-FOA counterselections, uracil and histidine were included at a concentration of 0.2 mM and 0.1%, respectively. The amount of 5-FOA included in the medium depends on the desired selection conditions. Concentrations between 0.2 mM and 2 mM have been used successfully. Both NM and YM medium can be used for the selections, although omitting adenine from the NM medium improves the tolerance of the cells to the minimal medium conditions. This is especially important for selections using 6 aza-uracil/URA3 reporter as a positive selection marker.

Figures 15A, 15B:
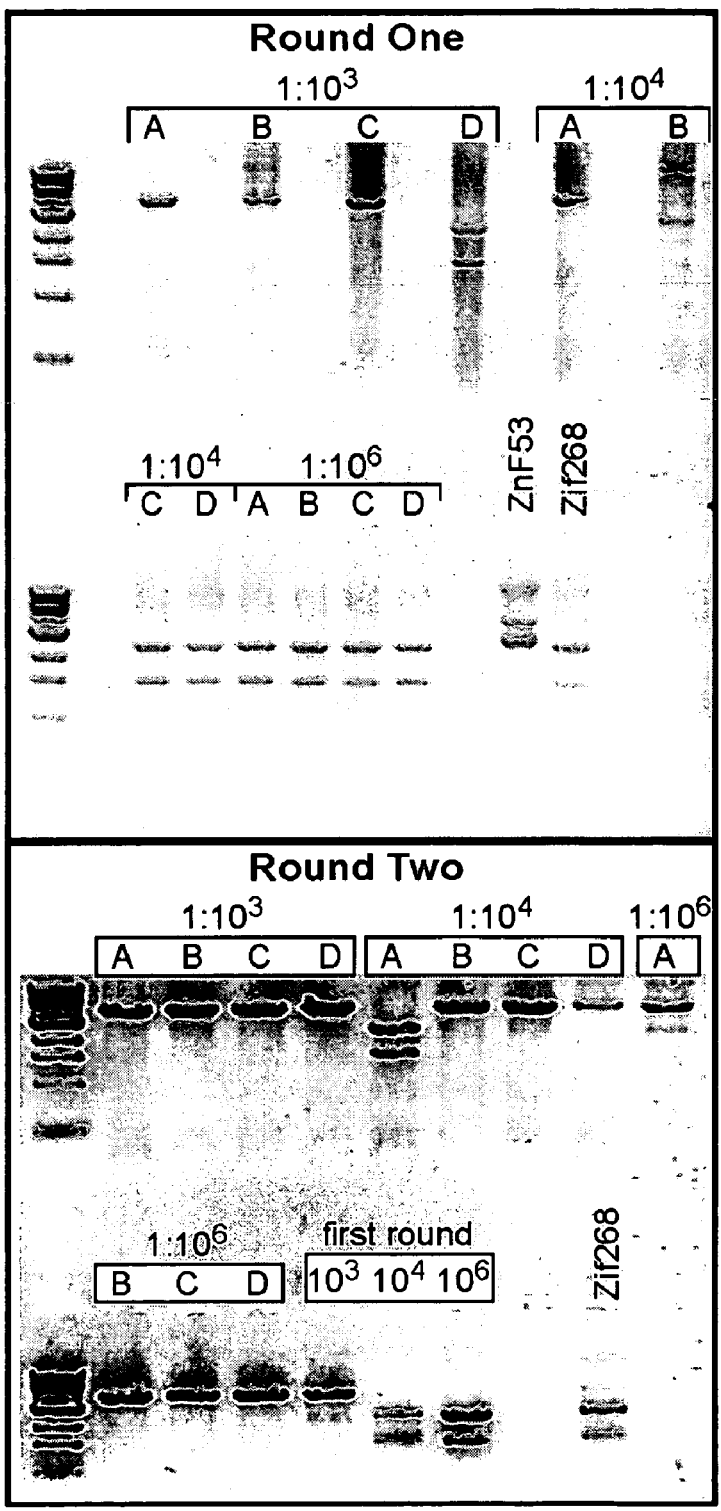
FIGS. 15A and 15B are representations of gels of restriction digests of baits isolated from the first and second rounds of mock selection.

Additional experiments were carried out to examine the ability of URA3 to be used as a counterselectable marker in a mock selection to distinguish between two $Cys_2His_2$ zinc finger DNA-binding domains (Zif268 and ZnF53) with different DNA-binding specificities (Wolfe et al. (1999) J. Mol. Biol., 285:1917-1934). The promoter of the URA3 reporter used in these selections contained a Zif268 binding site. This reporter was incorporated into the F' episome in the selection strain (Joung et al. (2000) Proc. Natl. Acad. Sci. USA, 97:7382-7387). The survival rate of cells containing either transcription factor Zif268 or ZnF53 (constructed as a bait by direct fusion to the alpha subunit of RNA polymerase) in the presence of the Zif268 URA3 reporter at various concentrations of 5-FOA with different minimal media recipes were compared. Interestingly, there was a difference in the effectiveness of 5-FOA depending on whether the cells are freshly transformed with the vector containing the transcription factor and challenged on 5-FOA minimal media or if the cells were allowed to first grow under rich media conditions and then single clones were amplified and challenged under the counterselection conditions, with the latter method being much more effective. The fresh transformation approach, which would correspond to a typical method for selection of desired constructs from a library of clones, was still effective, but the enrichment rate of undesired clones versus desired clones was ~1:$10^3$. In a mock selection after two rounds of counter-selection, using a ZnF53 bait diluted to a 1 in $10^6$ ratio, the presence of the Zif268 bait could be enriched in two rounds of selection on 0.2 mM 5-FOA/NM plates to dominate the final pool of clones (FIG. 15). Dilutions of the Znf53 bait in excess Zif286 bait were made at 1 in $10^3$, $10^4$, and $10^6$. These pools were transformed into a Zif286 URA3 reporter strain and selected at 0.2 mM 5-FOA.

Figure 16:
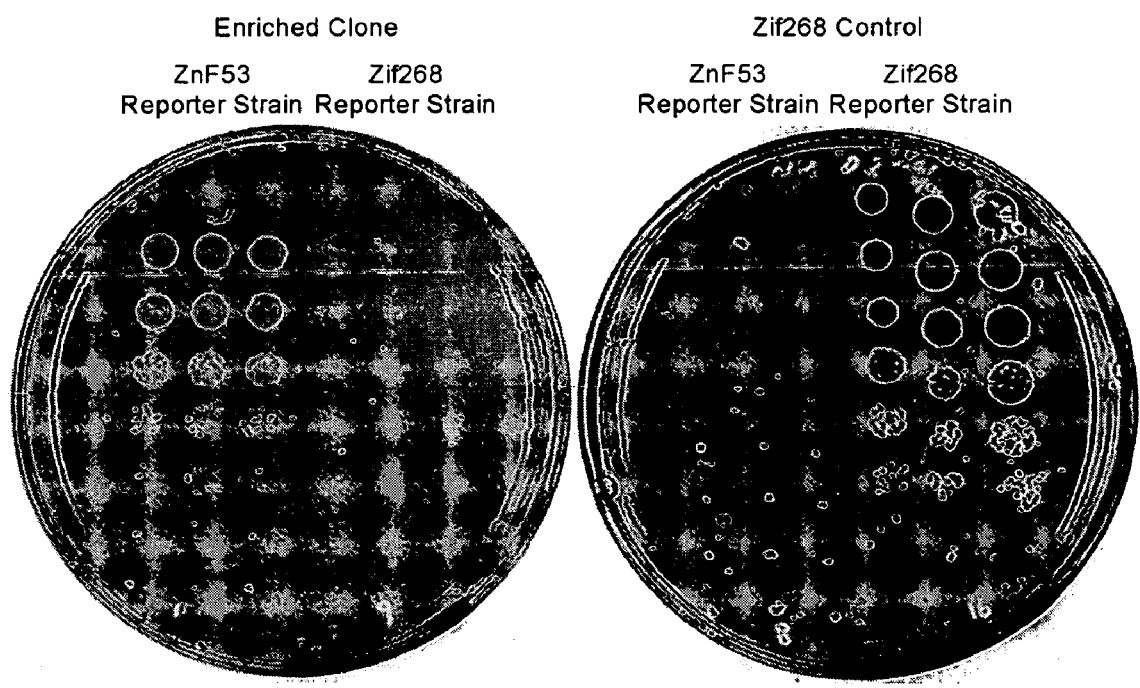
FIG. 16 is a representation of growth plates that show an analysis of a representative bait (ZnF53) enriched from a pool of primarily Zif268 baits following two rounds of 5-FOA counter-selection in a Zif268 reporter strain.

Cells were plated at a density of approximately $10^6$ cells on a 15 cm plate. Surviving colonies were harvested as a pool and their plasmid DNA was isolated and retransformed for a second round of selection. Four individual colonies from each selection after each round were isolated and assays by restriction digest (Aat2), which specifically cleaves Zif268 baits. After the first round of selection (FIG. 15A), the majority of the clones from the $10^3$ dilution were Znf53; however, the clones from the other higher dilutions were primarily (at $10^4$ dilution) or exclusively (at $10^6$ dilution) Zif268. After the second round of selection (FIG. 15B), the majority of the clones at all dilutions were Znf53. Note: single colonies from the pool of cells used in the second round of selection (plated on non-selective plates) were also picked and assayed to determine the bait that is present in clones prior to selection. The assayed colonies from the $10^4$ and $10^6$ pools contained Zif268 baits (first round). The putative Znf53 clones based on restriction digestion analysis that were isolated after two rounds of selection were confirmed by testing under positive selection conditions (6-aza uracil/NM plates) in bacterial strains that contained either a ZnF53 or Zif268 binding site upstream of the URA3 reporter. FIG. 16 shows a representative bait (ZnF53) enriched from a pool of primarily Zif268 baits following two rounds of 5-FOA counter-selection in a Zif268 reporter strain. The recovered bait (enriched clone) was reintroduced into a URA reporter strain containing either a ZnF53 (left 3 columns) or Zif268 (right 3 columns) binding site upstream of the promoter and these cells were challenged to grown at 0.2 µg/ml 6-aza uracil at 37 deg C. Robust growth was observed with the representative bait only in the ZnF53 reporter strain whereas a Zif268 bait grows robustly only in the presence of the Zif268 reporter strain. Cells were titred in 5-fold serial dilutions from top to bottom. Thus, counterselection can be used to enrich for the presence of a rare DNA binding protein.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining whether a test DNA molecule interacts with a test polypeptide, the method comprising
   (a) providing a first population of prokaryotic host cells, wherein at least one of the host cells comprises;
      (i) a reporter vector comprising a selectable reporter gene and a counterselectable reporter gene, wherein the selectable reporter gene and the counterselectable reporter gene are both operably linked to a test DNA molecule; and
      (ii) a chimeric gene that encodes a fusion protein comprising a test polypeptide fused to a gene activating domain, wherein interaction of the test DNA molecule and the test polypeptide in the host cell results in an increase in expression of the selectable reporter gene and of the counterselectable reporter gene;
   (b) maintaining the first population of host cells under selective conditions that allow cell growth as a result of the expression of the selectable reporter gene;
   (c) isolating the reporter vectors from cells of the first population of host cells that grow under the selective conditions;
   (d) introducing the isolated reporter vectors into a second population of host cells that lack the chimeric gene;
   (e) maintaining the second population of host cells under counterselective conditions that inhibit cell growth as a result of the expression of the counterselectable reporter gene; and
   (f) measuring growth of the second population of host cells, wherein an ability to survive under counterselective conditions indicates that the test DNA molecule has interacted with the test polypeptide.

2. The method of claim 1, further comprising identifying a test DNA molecule that interacts with the test polypeptide, the method comprising isolating a reporter vector from a cell of the second population of host cells that grow under the counterselective conditions; and determining the sequence of the test DNA molecule in the reporter vector.

3. The method of claim 1, wherein the test DNA molecule is from a nucleic acid library.

4. The method of claim 1, wherein the host cells lack a functional endogenous gene that is functionally homologous to the selectable reporter gene, and wherein the host cell is not capable of growing under selective conditions in the absence of the selectable reporter gene.

5. The method of claim 1, wherein the host cells lack a functional endogenous his-B gene.

6. The method of claim 1, wherein the host cells lack a functional endogenous gene that is functionally homologous to the counterselectable reporter gene, and wherein the host cell is capable of growing under counterselective conditions in the absence of the counterselectable reporter gene.

7. The method of claim 1, wherein the host cells lack a functional endogenous pyrF gene.

8. The method of claim 1, wherein the selectable reporter gene is selected from the group consisting of LEU2, TRP1, and HIS3.

9. The method of claim 8, wherein the selectable reporter gene is HIS3 and the selective conditions comprise maintaining the host cells in medium lacking histidine.

10. The method of claim 9, wherein the selective conditions further comprise maintaining the host cells in medium comprising 3-amino-1, 2, 4-triazole (3-AT).

11. The method of claim 1, wherein the counterselectable reporter gene is selected from the group consisting of URA3, LYS2, GAL1, CYH2, sacB, and CAN1.

12. The method of claim 11, wherein the counterselectable reporter gene is URA3 and the counterselective conditions comprise maintaining the host cells in medium comprising uracil and 5-fluoro orotic acid (5-FOA).

13. The method of claim 1, wherein the reporter gene encodes a gene product that provides at least one detectable signal selected from the group consisting of color, fluorescence, luminscence, a cell surface tag, cell viability, relief of a cell nutritional requirement, cell growth, and drug resistance.

14. The method of claim 1, wherein the reporter gene encodes a gene product selected from the group consisting of a spectinomycin resistance gene product, a streptomycin resistance gene, chloramphenicol acetyl transferase, luciferase, β-galactosidase, and alkaline phosphatase.

15. The method of claim 1, wherein the host cell is selected from the group consisting of a strain of *Escherichia, Bacillus, Streptomyces, Pseudomonas, Salmonella, Serratia,* and *Shigella.*

16. The method of claim 1, wherein the gene activating domain comprises the α domain of RNA polymerase.

17. The method of claim 1, wherein the selectable reporter gene and the counterselectable reporter gene are operably linked to a lac promoter.

* * * * *

UNITED STATES PATENT AND TRADEMARK OFFICE
CERTIFICATE OF CORRECTION

| | | |
|---|---|---|
| PATENT NO. | : 7,504,216 B2 | Page 1 of 1 |
| APPLICATION NO. | : 11/050174 | |
| DATED | : March 17, 2009 | |
| INVENTOR(S) | : Wolfe et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 268 days.

Delete the phrase "by 268 days" and insert -- by 677 days --

Signed and Sealed this

Fifteenth Day of June, 2010

David J. Kappos
*Director of the United States Patent and Trademark Office*